United States Patent [19]

Schally et al.

[11] Patent Number: 5,258,492
[45] Date of Patent: *Nov. 2, 1993

[54] LHRH ANALOGUES WITH CYTOTOXIC MOIETIES AT THE SIXTH POSITION

[75] Inventors: Andrew V. Schally, Metarie, La.; Sandor Bajusz, Budapest, Hungary

[73] Assignee: The Administrators of the Tulane Educational Fund, New Orleans, La.

[ * ] Notice: The portion of the term of this patent subsequent to Dec. 15, 2009 has been disclaimed.

[21] Appl. No.: 710,515

[22] Filed: Jun. 3, 1991

Related U.S. Application Data

[63] Continuation of Ser. No. 404,667, Sep. 7, 1989, abandoned, which is a continuation-in-part of Ser. No. 260,994, Oct. 21, 1988, abandoned.

[51] Int. Cl.$^5$ .......................... C07K 7/20; C07K 7/06
[52] U.S. Cl. .................................. 530/313; 530/328; 530/816; 530/810; 424/85.9; 424/85.91; 930/110
[58] Field of Search ............... 530/313, 328, 816, 810; 514/15, 800; 424/85.9, 85.91; 930/110

[56] References Cited

U.S. PATENT DOCUMENTS 4,115,418 9/1978 Gale et al. ............................ 424/287
4,761,398 8/1988 Edens et al. ........................... 514/15

FOREIGN PATENT DOCUMENTS 0127108 12/1984 European Pat. Off. ............ 530/342
0041377 4/1974 Japan ................................. 530/313

OTHER PUBLICATIONS

Jennes et al, Peptides, vol. 7, pp. 459–463, (1986).
Folkers et al, Chem. Abs., vol. 97 (13), 104360m, (1982).
Bajusz et al, Chem. Abs., vol. 112 (1), 790 p, (1989).
Hocart et al, Chem. Abs., vol. 101 (3), 17549n, (1983).
Rosenberg et al, Nature, vol. 222, Apr. 26 1969, pp. 385–386.
Maier, Naturwissenschaften, vol. 74 (1987), pp. 374–382.

Primary Examiner—Merrell C. Cashion, Jr.
Assistant Examiner—T. Wessendorf
Attorney, Agent, or Firm—Omri M. Behr; Matthew J. McDonald

[57] ABSTRACT

The present invention deals with LHRH analogues which contain cytotoxic moieties and have influence on the release of gonadotropins from the pituitary gland of mammals, including humans. The compounds of this invention are represented by the formula:

$$X-R^1-R^2-R^3-Ser-R^5-R^6(Q)-Leu-Arg-Pro-R^{10}-NH_2$$

wherein
$R^1$ is pGlu, Pro, D-Nal(2), or D-Phe(4Cl),
$R^2$ is His or D-Phe(4Cl),
$R^3$ is Trp, D-Trp or D-Pal(3),
$R^5$ is Tyr or Arg,
$R^6$ is D-Phe or $R^{*6}$, where $R^{*6}$ is D-Orn, D-Lys or D-Phe(NH$_2$),
$R^{10}$ is Gly or D-Ala,
X is hydrogen, a lower alkanoyl group of 2-5 carbon atoms or carbamyl,
Q is bis-(2-chloroethyl)amino group provided that $R^6$ is D-Phe,
where $R^6$ is $R^{*6}$,
Q is a complexed metal-containing acyl group having the formula:

$$[(Q')(A)] \text{ or } [(Q'')(B)_2(A)]$$
$$\text{II} \qquad \qquad \text{III}$$

wherein
Q' is Pt(Y)$_2$, where Y is an anion derived from a pharmaceutically acceptable acid,
A is a diaminoacyl group having the formula $$\underset{NH_2}{\overset{}{CH_2(CH_2)_m}}-\underset{NH_2}{\overset{}{CH}}-(CH_2)_{\overline{n}}CO-NH-(CH_2)_{\overline{o}}CO-{}_{\overline{p}} \qquad \text{IV}$$

where
m is 0 or 1,
n and p are 0–10, (Abstract continued on next page.)

o is 1-10,

Q″ is a non-platinum-group metal, either a main-group metal such as gallium, germanium, and tin, or a transition metal such as titanium, vanadium, iron, copper, cobalt, gold, nickel, cadmium and zinc, B is a aralkylidene, heteroaralkylidene, cycloalkylidene or heterocycloalkylidene group containing oxygen anion or carboxylate anion at position 2 or 3, and pharmaceutically acceptable salts thereof and methods of use pertaining these compounds.

5 Claims, No Drawings

LHRH ANALOGUES WITH CYTOTOXIC MOIETIES AT THE SIXTH POSITION

This invention was made with Government support under Grant Nos. 2RD1 CA40003 and CA40004, awarded by the N.C.I. (NIH). The U.S. Government has certain rights in this application.

This application is a continuation of application Ser. No. 07/404,667, filed Sep. 7, 1989 which was a continuation in part of application Ser. No. 07/260,994 filed Oct. 21, 1988, both now abandoned.

The present invention relates to novel peptides which contain cytotoxic moieties and have influence on the release of gonadotropins from the pituitary in mammals, including humans. More specifically, the present invention relates to analogues of luteinizing hormone-releasing hormone (LHRH), which have the structure:

pGlu-His-Trp-Ser-Tyr-Gly-Leu-Arg-Pro-Gly-NH$_2$ salts thereof, and to pharmaceutical compositions and methods of use pertaining to these analogues.

DISCUSSION OF THE PRIOR ART

Hypothalamic luteinizing hormone-releasing hormone (LHRH) controls pituitary synthesis of gonadotropins (LH and FSH) that stimulate the synthesis of sex steroids in the gonads.

Many analogues of this hormone have been prepared and studied in order to find molecule(s) with sufficient biological activity to be clinically useful.

Significant enhancement of the LH-releasing potency has been obtained by introducing D-amino acids in place of Gly at position 6 and in some analogues also by modification at position 10.

The superagonist analogues of LHRH involved in clinical development are represented by general formula A wherein the combination of residues $R^6$ and $R^{10}$ are as follows:

A pGlu-His-Trp-Ser-Tyr-$R^6$-Leu-Arg-Pro-$R^{10}$

A1 (Leuprolid), $R^6$ is D-leu, $R^{10}$ is NH-Et;

J. A. Vilchez-Martinez et al., Biochem. Biophys. Res. Commun., 59, 1226–1232 (1974).

A2 (Decapeptidyl), $R^6$ is D-Trp, $R^{10}$ is Gly-NH$_2$;

D. H. Coy et al., J. Med. Chem., 19, 423–425 (1976).

A3 (Buserelin), $R^6$ is D-Ser(tBu), $R^{10}$ is NH-Et;

W. Koenig et al., In: R. Walter and J. Meienhofer (eds.), Peptides: Chemistry, Structure and Biology. Proceedings of the Fourth American Peptide Symposium. Ann Arbor Science, Ann Arbor, Mich., 1975, pp. 883–888.

A4 (Zoladex, ICI-118630), $R^6$ is D-Ser(tBu), $R^{10}$ is NH—NH—CO—NH$_2$;

A. S. Dutta et al., J. Med. Chem., 21, 1018–1024 (1978).

A5 (Nafarelin), $R^6$ is D-Nal(2), $R^{10}$ is Gly-NH$_2$;

J. J. Nestor et al., J. Med. Chem. 25, 795–801 (1982).

In addition to agonists, analogues have been prepared which are competitive antagonists to LHRH. In these analogues, agonist activity is reduced by aromatic D-amino acid substitutions at positions 2 and 3, and receptor affinity is retained by replacements at positions 1 and 6, in some analogues, also 10, and by acylation of the peptide N-terminus. It has also been shown that replacement of Tyr$^5$ by basic residues, such as Arg, in combination with a hydrophobic residue at position 6 is helpful. Most of the highly potent antagonists of LHRH are represented by general formula B wherein the combination of residues $R^3$, $R^5$, $R^6$, and $R^8$ are as follows:

Ac-D-Nal(2)-D-Phe(4Cl)-$R^3$-Ser-$R^5$—$R^6$-Leu-$R^8$-Pro-D-Ala-NH$_2$    B.

B1, $R^3$ is D-Trp, $R^5$ is Tyr, $R^6$ is D-Arg, and $R^8$ is Arg;

A. Horvath et al., Peptides, 3, 969–971 (1982).

B2, $R^3$ is D-Pal(3), $R^5$ is Arg, $R^6$ is D-Glu(AA), i.e. 4-(p-methoxybenzoyl)-D-2-aminobutyric acid, and $R^8$ is Arg;

J. E. Rivier et al., J. Med. Chem., 29, 1846–1851 (1986).

B3, $R^3$ is D-Pal(3), $R^5$ is Lys(nicotinyl), $R^6$ is D-Lys(nicotinyl) and $R^8$ is Lys(isopropyl);

A. Ljungqvist et al., Biochem. Biophys. Res. Commun., 148, 849–856 (1987).

B4, $R^3$ is D-Trp or D-Pal(3), $R^5$ is Tyr, $R^6$ is D-Cit or D-Hci, and $R^8$ is Arg;

S. Bajusz et al., Proc. Natl. Acad. Sci. USA, 85, 1637–1641 (1988); U.S. patent application Ser. No. 197,153, filed May 23, 1988 which co-pending application is a continuation-in-part of U.S. patent application Ser. No. 07/074,126, filed Jul. 17, 1987 issued as U.S. Pat. No. 4,800,191.

It has been revealed that chronic administration of superagonist analogues of LHRH is at first associated with the expected increase in gonadotropin and steroid secretion, then it leads to the inhibition of pituitary and gonadal functions, to wit, to chemical castration [J. Sandow at al., Fertil. Steril., 20, 205–209 (1978); A. J. W. Hsueh and G. F. Erickson, Science, 204, 854 (1979)]. LHRH antagonists exert the same effects but of course, without causing initial stimulation.

In accordance with the above, LHRH superagonist A4 has been found to be as effective as ovariectomy in treatment of rat mammary carcinomas, which is known to contain estrogen receptors [R. I. Nicholson and P. V. Maynard, Br. J. Cancer, 39, 268–273 (1979)]. Furthermore, LHRH superagonists, such as A2, have been reported to be of value in treating patients with certain hormone-dependent tumors, such as breast and prostatic cancers [A. V. Schally et al., Cancer Treat. Rep., 68, 281 (1984); H. Parmar et al., Lancet, 2, 1201 (1985)].

Remission of breast or prostate tumor growth after LHRH agonist (A4) administration is apparently mediated by suppression of gonadotropin secretion and the resultant decrease of gonadal steroid hormone secretion [R. I. Nicholson et al., J. Steroid Biochem., 20, 129 (1984)].

Since remission of tumor growth has also been observed in postmenopausal women (in whom ovarian steroid production is minimal) it is supposed that these peptides act directly on breast tumor cells [H. A. Harvey et al., Proc. Am. Assoc. Cancer Res. Am. Soc. Clin. Oncol. 22, 436 (1981)].

In vitro studies have also suggested that LHRH agonists and antagonists may act directly on cancer cells. Namely, it has been demonstrated that certain human breast carcinoma cells contain binding sites for LHRH [K. A. Eidne et al., Science 229, 989–991 (1985)] and that the growth of such cells can be inhibited by LHRH agonist A3 [W. R. Miller et al., Nature 313, 231–233 (1985)]. Another study has revealed that certain LHRH antagonists (e.g. the D-alpha-Me-4-Cl-Phe analogue of B1) bind to several breast cancer cell lines and inhibit incorporation of [$^3$H]thymidine into DNA as well as tumor growth [K. A. Eidne et al., J. Clin. Endocr. Metab. 64, 425-432 (1987)]. Our recent, still unpublished findings have revealed that both agonistic and antagonistic analogues of LHRH bind to human breast cancer cell membranes, and also to the cell membranes of pancreatic tumor which are known to be hormone-independent.

In spite of the above, clinical studies have shown that the duration of remission of tumor growth may be limited as hormonal manipulations do not prevent the ultimate growth of hormone-independent cells [J. T. Isaacs and D. S. Coffey, Cancer Res. 41, 5070-5075 (1981)]. Combination of hormonal therapy with chemotherapy could forestall this phenomenon and prolong survival [J. T. Isaacs, Prostate 5, 1-17 (1984)].

It is especially desirable, in view of this, to provide LHRH analogues which contain cytotoxic moieties. Such compounds can exert the direct or indirect antitumor effects of LHRH agonists or antagonists and, at the same time, act as chemotherapeutic agents targeted to the tumor cells by the peptide portions for which binding sites are present on the cell membranes.

Three LHRH analogues having a cytotoxic moiety, an agonist and two antagonists, have been synthesized so far. In these molecules, Chlorambucil, 4-[4-(bis[2-chloroethyl] amino)phenyl]butyric acid, is linked to complete decapeptide sequences and a nonapeptide fragment, respectively. The agonist analogue, [D-Lys(-Chlorambucil)$^6$] LHRH [K. Channabasavaiah and J. M. Stewart, Biochem. Biophys. Res. Commun., 86, 1266-1273 (1979)] and one of the antagonists, [Chlorambucil-D-Leu$^2$,D-Leu$^3$,D-Ala$^6$]LHRH (2-10) [C. Y. Bowers et al., Biochem. Biophys. Res. Commun., 61, 698-703 (1974)] showed moderate activities, and the other antagonist, [Chlorambucil-D-Phe$^1$,D-Phe$^2$,D-Trp$^{3,6}$]LHRH [K. Channabasavaiah et al., In: E. Gross and J. Meienhofer (eds.), Peptides, Proceedings of the Sixth American Peptide Symposium, Pierce Chem. Co. Rockford, Ill., 1979, pp 803-807] was practically inactive.

The peptides of Formula I (X—R$^1$—R$^2$—R$^3$-Ser-R$^5$—R$^6$(Q)-Leu-Arg-Pro-R$^{10}$—NH$_2$, see below) of the present invention wherein residue R$^{*6}$ carries [Q''(B)$_2$(A)] as cytotoxic moiety, can be related to certain cytotoxic organometallic compounds which have recently been reviewed by P. Kopf-Maier [Naturwissenschaften 74, 374-382 (1987)]. For example, a moiety [(Q'')(B)$_2$(A)] wherein Q'' is Cu$^{++}$, B is derived from salicylaldehyde, and A is a 2,3 or 2,4-diamino acid residue, is related to the cytotoxic trans-bis(salicylaldoximato) copper(II) [H. O. Elo and P. O. Lumme, Cancer Treat. Rep. 69, 1021-1022 (1985)]. Moieties [(Q'')(B)$_2$(A)] can also comprise B residues which are derived from hydroxy-oxo-compounds possessing cytotoxic activity in their own right. Such hydroxy-oxo-compounds incorporated into [(Q'')(B)$_2$(A)] by means of Q'' and A are, for example, pyridoxal 5-phosphate which is a selective inhibitor of oncoviral DNA polymerase [M. J. Modak, Biochem. Biophys. Res. Commun. 71, 180-187 (1976)]. Similarly, in peptides of Formula I of the present invention, moieties [(PtCl$_2$)(A)] linked to the peptide portion of the compounds of the present invention, are related to the known cytotoxic platinum compounds such as cis-diaminedichloro platinum(II) ("Cisplatin") [B. Rosenberg et al., Nature 222, 385 (1969)].

SUMMARY OF THE INVENTION

The present invention deals with LHRH analogues which possess high agonistic or antagonistic effect and comprise cytotoxic moieties, such as nitrogen mustard, platinum complexes or complexes of metals derived from the non-platinum-group metal antitumor agents which are represented by inorganic or organometallic compounds containing either main-group metals such as gallium, germanium, and tin, or transition metals such as titanium, vanadium, iron, copper, cobalt and gold, and also nickel, cadmium and zinc, or a cytotoxic compound incorporated as a complex of the above-mentioned metals.

The compounds of this invention are represented by Formula I

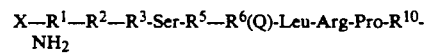

wherein

R$^1$ is pGlu, Pro, D-Nal(2), or D-Phe(4Cl),

R$^2$ is His or D-Phe(4Cl),

R$^3$ is Trp, D-Trp or D-Pal(3),

R$^5$ is Tyr or Arg,

R$^6$ is D-Phe or R$^{*6}$, where R$^{*6}$ is D-Orn, D-Lys or D-Phe(NH$_2$),

R$^{10}$ is Gly or D-Ala,

X is hydrogen, a lower alkanoyl group of 2-5 carbon atoms or carbamyl,

Q is bis-(2-chloroethyl)amino group provided that R$^6$ is D-Phe, where R$^6$ is R$^{*6}$, Q is an acyl group having the formula

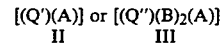

wherein

Q' is Pt(Y)$_2$, where Y is an anion of a pharmaceutically acceptable acid,

A is a diaminoacyl group having the formula

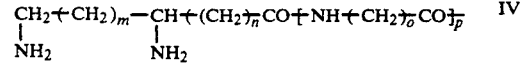

where m is 0 or 1, n and p are 0-10, o is 1-10,

Q'' is a non-platinum-group metal, either a main-group metal such as gallium, germanium, and tin, or a transition metal such as titanium, vanadium, iron, copper, cobalt, gold, nickel, cadmium and zinc, B is aralkylidene, heteroaralkylidene, cycloalkylidene or heterocycloalkylidene group containing oxygen anion or carboxylate anion.

Suitably, there are used phenyl loweralkylidenes substituted by halo or nitro, preferrably chloro or fluoro; lower alkylpyridyl lower alkylidenes, suitably substituted by hydroxy methyl or phosphoxymethyl; furanyl lower alkylidenes, optionally substituted by one or two lower alkyl moieties and, if desired, cycloalkyl lower alkylidines of 5 to 7 carbon atoms in the ring, optionally substituted by one or two lower alkyl moieties; all of the above cyclic moieties being substituted by hydroxy or carboxy. In other words, B may be (G)-2—benzylidene where G is hydrogen, fluoro, chloro or nitro, $(R_{12})$-5,6-dihydro-4-O-3-furylidene where $R_{12}$ is methyl or hydrogen and q is 0, 1 or 2, $(R_{12})$-2-COO—cyclopentylidene where $R_{12}$ is methyl or hydrogen and q is 0 1 or 2, or (J)-3-O—4-picolylidene.

Especially preferred are those cyclic compounds in which the substituting oxygen containing function is at position 2 or 3, where it exerts cytotoxic activity either by itself or in combination with the metal, and which is derived from a 2- or 3-hydroxy or carboxy-1-oxo-compound such as substituted or unsubstituted salicylaldehyde, pyridoxal, 4-hydroxy- 3-furanone or a 1- or 2-carboxy-cycloalkane of 5-7 carbon atoms that forms a Schiff base with the amino group of A and can combine with a metal ion through its negatively charged oxygen or carboxylate. The preferred cyclic compound may be represented by any of the Formulas $B_1$–$B_4$:

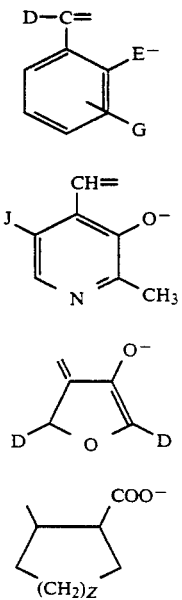

wherein
D is methyl or hydrogen,
E is $O^-$ or $COO^-$,
G is fluoro, chloro or nitro,
J is hydroxymethyl or phosphoxymethyl,
z is 1, 2 or 3.

The compounds of Formula I can be prepared by a combination of the solid phase technique and the classical (solution) synthesis.

Preferably, the compounds of Formula I wherein $R^6$ is D-Phe [carrying the bis-(2-chloroethyl)amino group] are prepared by condensation of pentapeptide fragments (1-5) and (6-10).

Compounds of Formula I wherein $R^6$ is $R^{*6}$ are preferably prepared from intermediate peptides of Formula V:

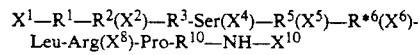

wherein
$R^1$, $R^2$, $R^3$, $R^5$, $R^{*6}$ and $R^{10}$ are as defined hereinabove, $X^1$ is a lower alkanoyl group of 2-5 carbon atoms or carbamyl, or provided that $R^1$ is pGlu, $X^1$ is hydrogen, $X^2$ is nil or a protecting group for the His imidazole nitrogen, $X^4$ is hydrogen or a protecting group for the Ser hydroxyl group, $X^5$ is hydrogen or a protecting group for the Tyr phenolic hydroxyl group, or a protecting group for the guanidino group of Arg, $X^6$ is hydrogen or a protecting group for the Lys, Orn or Phe($NH_2$) side chain amino group, $X^8$ is hydrogen or a protecting group for the Arg guanidino group, $X^{10}$ is hydrogen or benzhydryl group incorporated into a resin.

The intermediate peptides of Formula V are preferably synthesized by the solid phase method. The ensuing peptides of Formula V wherein $X^2$, $X^4$, $X^5$, $X^6$, $X^8$, and $X^{10}$ are hydrogen, are then acylated with suitably protected A, to yield, after deprotection, intermediate peptides of Formula VI:

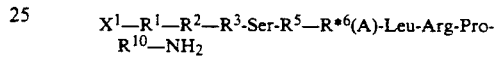

wherein
$X^1$, $R^1$, $R^2$, $R^3$, $R^5$, $R^{*6}$, $R^{10}$ and A are as defined hereinabove.

According to another suitable method, intermediate peptides of Formula VI are obtained by deprotection of intermediate peptides of Formula VIA

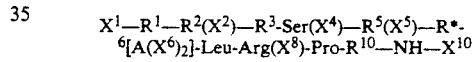

wherein
$R^1$, $R^2$, $R^3$, $R^5$, $R^{*6}$, $R^{10}$, A, $X^1$, $X^2$, $X^4$, $X^5$, $X^6$, $X^8$, and $X^{10}$ are as defined hereinabove, which in turn are prepared by the same solid phase method as the intermediate peptides of Formula V with the exception that suitably protected $R^{*6}[A(X^6)_2]$ is incorporated in place of suitably protected $R^{*6}(X^6)$ in position 6.

The process of preparing the Formula I compounds comprises reaching a peptide of Formula VI with $K_2PtCl_4$ to obtain a peptide of Formula I wherein residue $R^{*6}$ carries $[(PtCl_2)(A)]$ as cytotoxic moiety which, if desired, can be converted into $[(PtY_2)(A)]$ by known methods.

Alternatively, the process comprises reacting a peptide of Formula VI with a hydroxy- (or carboxyl-) oxo compound and a non-platinum-group metal, as an acetate salt, or with the complex compound they form to yield a peptide of Formula I.

A pharmaceutical composition is provided by admixing the compound of Formula I with pharmaceutically acceptable carrier including microcapsules (microspheres) for delayed delivery.

There is also provided a method for relieving complications resulting from the physiological availability of amounts of pituitary gonadotropins in a mammal, in excess of the desired amount, which involves administering to the mammal a gonadotropin antagonizing dose of the compound of formula I.

DESCRIPTION OF THE PREFERRED EMBODIMENTS

For convenience in describing this invention, the conventional abbreviations for the amino acids, peptides and their derivatives are used as generally accepted in the peptide art and as recommended by the IUPAC-IUB Commission on Biochemical Nomenclature [European. J. Biochem., 138, 9–37 (1984)].

The abbreviations for the individual amino acid residues are based on the trivial name of the amino acid, e.g. pGlu is pyroglutamic acid, His is histidine, Trp is tryptophane, Ser is serine, Tyr is tyrosine, Lys is lysine, Orn is ornithine, Leu is leucine, Arg is arginine, Pro is proline, Gly is glycine and Ala is alanine, Phe is phenylalanine. Where the amino acid residue has isomeric forms, it is the L-form of the amino acid that is represented unless otherwise expressly indicated. Abbreviations of the uncommon amino acids employed in the present inventions are as follows: D-Mel is 4-[bis(2-chloroethyl)amino]-D-phenylalanine, $A_2bu$ is 2,4-diaminobutyric acid, $A_2pr$ is 2,3-diaminopropionic acid, Nal(2) is 3-(2-naphthyl)alanine, D-Pal(3) is 3-(3-pyridyl)alanine, Phe(NH$_2$) is 4-aminophenylalanine, Phe(4Cl) is 4-chlorophenylalanine.

Peptide sequences are written according to the convention whereby the N-terminal amino acid is on the left and the C-terminal amino acid is on the right.

Other abbreviations used are:
AcOH: acetic acid
Ac$_2$O: acetic anhydride
Boc: tert.butoxycarbonyl
Bzl: benzyl
CISAL: 5-chloro-2-O⁻-1-benzylidene
DCB: 2,6-dichlorobenzyl
DCC: N,N'-dicyclohexylcarbodiimide
DIC: N,N'-diisopropylcarbodiimide
DIEA: N,N-diisopropylethylamine
DMF: dimethylformamide
Eac: 6-amino-caproyl
FUR: 5,6-dihydro-2,5-dimethyl-4-O⁻-3-furylidene
HOBt: 1-hydroxybenzotriazole
HODNP: 2,4-dinitrophenol
HOPCP: pentachlorophenol
HPLC: high performance liquid chromatography
IpOH: isopropyl alcohol
MeCN: acetonitrile
MeOH: methyl alcohol
PEN: 2-COO⁻-cyclopentylidene
POL: 2-methyl-3-O⁻-5-hydroxymethyl-4-picolylidene
POLP: 2-methyl-3-O⁻-5-phosphooxymethyl-4-picolylidene
SAL: 2-O⁻-1-benzylidene
TEA: triethylamine
TFA: trifluoroacetic acid
Tos: 4-toluenesulfonyl
Z(2-Cl): 2-chloro-benzyloxycarbonyl
Z: benzyloxycarbonyl.

Especially preferred are LHRH analogues of Formula I

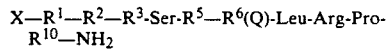

wherein,
$R^1$ is D-Nal(2), D-Phe(4Cl),
$R^2$ is D-Phe(4Cl),
$R^3$ is D-Trp or D-Pal(3),
$R^5$ is Tyr or Arg,
$R^6$ is D-Phe or $R^{*6}$, where D-Lys or D-Orn,
$R^{10}$ is D-Ala,
X is acetyl.

Also preferred is the peptide series where $R^1$ is pGlu, $R^2$ is His, $R^3$ is Trp, $R^5$ is Tyr, $R^6$ is as defined hereinabove, $R^{10}$ is Gly, and X is hydrogen.

With respect to the remaining preferred moieties: Q is bis-(2-chloroethyl)amino group provided that $R^6$ is D-Phe; where $R^6$ is $R^{*6}$, Q is an acyl group having the formula

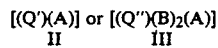

wherein
Q' is PtCl$_2$,
A is L,D-$A_2$pr, L,D-$A_2$bu, L,D-$A_2$pr-Eac or DL-$A_2$bu-Eac,
Q" is Cu++ or Ni++,
B is SAL, CISAL, POL, POLP, FUR or PEN, The most particularly preferred embodiments are:
1, pGlu-His-Trp-Ser-Tyr-D-Mel-Leu-Arg-Pro-Gly-NH$_2$,
2, Ac-D-Nal(2)-D-Phe(4Cl)-D-Pal(3)-Ser-Arg-D-Mel-Leu-Arg-Pro-D-Ala-NH$_2$
3, pGlu-His-Trp-Ser-Tyr-D-Lys[(PtCl$_2$)(DL-A$_2$pr)]-Leu-Arg-Pro-Gly-NH$_2$,
4, Ac-D-Phe(4Cl)-D-Phe(4Cl)-D-Trp-Ser-Tyr-D-Lys[(PtCl$_2$) (DL-A$_2$pr)]-Leu-Arg-Pro-D-Ala-NH$_2$
5, Ac-D-Nal(2)-D-Phe(4Cl)-D-Trp-Ser-Arg-D-Lys[(PtCl$_2$) (DL-A$_2$pr)]-Leu-Arg-Pro-D-Ala-NH$_2$,
6, pGlu-His-Trp-Ser-Tyr-D-Lys[(Cu++)(SAL)-$_2$(A$_2$pr)]-Leu-Arg-Pro-Gly-NH$_2$,
7, pGlu-His-Trp-Ser-Tyr-D-Lys[(Cu++)(SAL)$_2$(D-A$_2$pr)]-Leu-Arg-Pro-Gly-NH$_2$
8, pGlu-His-Trp-Ser-Tyr-D-Lys[(Ni++)(SAL)-$_2$(A$_2$pr)]-Leu-Arg-Pro-Gly-NH$_2$,
9, pGlu-His-Trp-Ser-Tyr-D-Lys[(Ni++)(SAL)$_2$(D-A$_2$pr)]-Leu-Arg-Pro-Gly-NH$_2$
10, pGlu-His-Trp-Ser-Tyr-D-Lys[(Cu++)(CISAL)-$_2$(A$_2$pr)]-Leu-Arg-Pro-Gly-NH$_2$
11, pGlu-His-Trp-Ser-Tyr-D-Lys[(Ni++)-(CISAL)$_2$(DL-A$_2$pr)]-Leu-Arg-Pro-Gly-NH$_2$
12, Ac-D-Nal(2)-D-Phe(4Cl)-D-Pal(3)-Ser-Arg-D-Lys[(Cu++) (SAL)$_2$(DL-A$_2$pr)]-Leu-Arg-Pro-D-Ala-NH$_2$,
13, Ac-D-Nal(2)-D-Phe(4Cl)-D-Trp-Ser-Arg-D-Lys[(Cu++) (SAL)$_2$(DL-A$_2$pr)]-Leu-Arg-Pro-D-Ala-NH$_2$,
14, Ac-D-Nal(2)-D-Phe-(4Cl)-D-Pal(3)-Ser-Arg-D-Lys[(Ni++) (SAL)$_2$(DL-A$_2$pr)]-Leu-Arg-Pro-D-Ala-NH$_2$,
15, pGlu-His-Trp-Ser-Tyr-D-Lys[(Cu++)(SAL)$_2$(DL-A$_2$bu)]-Leu-Arg-Pro-Gly-NH$_2$
16, Ac-D-Nal(2)-D-Phe(4Cl)-D-Trp-Ser-Arg-D-Lys[(Ni++) (SAL)$_2$(DL-A$_2$pr)]-Leu-Arg-Pro-D-Ala-NH$_2$,
17, pGlu-His-Trp-Ser-Tyr-D-Lys[(Cu++)-(POLP)$_2$(LD-A$_2$bu)]-Leu-Arg-Pro-Gly-NH$_2$
18, pGlu-His-Trp-Ser-Tyr-D-Lys[(Cu++)(FUR)$_2$(DL-A$_2$pr)]-Leu-Arg-Pro-Gly-NH$_2$, 19, pGlu-His-Trp-Ser-Tyr-D-Lys[(Cu++)(POL)$_2$(DL-A$_2$pr)]-Leu-Arg-Pro-Gly-NH$_2$ 20, pGlu-His-Trp-Ser-Tyr-D-Lys[(Cu++)(POLP)$_2$(A$_2$pr)]-Leu-Arg-Pro-Gly-NH$_2$ 21, Ac-D-Nal(2)-D-Phe(4Cl)-D-Pal(3)-Ser-Arg-D-Lys[(Cu++) (POLP)$_2$(DL-A$_2$pr)]-Leu-Arg-Pro-D-Ala-NH$_2$, 22, pGlu-His-Trp-Ser-Tyr-D-Lys[(Cu++)(PEN)$_2$(A$_2$pr)]-Leu-Arg-Pro-Gly-NH$_2$ 23, Ac-D-Nal(2)-D-Phe(4Cl)-D-Trp-Ser-Arg-D-Lys[-(Cu++) (POLP)$_2$(DL-A$_2$pr)]-Leu-Arg-Pro-D-Ala-NH$_2$, 24, Ac-D-Nal(2)-D-Phe(4Cl)-D-Trp-Ser-Arg-D-Lys[-(Cu++) (POL)$_2$(DL-A$_2$pr)]-Leu-Arg-Pro-D-Ala-NH$_2$, 25, Ac-D-Nal(2)-D-Phe(4Cl)-D-Pal(3)-Ser-Arg-D-Lys[(Cu++)(POL)$_2$(DL-A$_2$pr)]-Leu-Arg-Pro-D-Ala-NH$_2$, 26, pGlu-His-Trp-Ser-Tyr-D-Lys[(Cu++)(POL)$_2$(DL-A$_2$bu)]-Leu-Arg-Pro-Gly-NH$_2$ 27, pGlu-His-Trp-Ser-Tyr-D-Lys[(Cu++)(SAL)$_2$(DL-A$_2$bu-Eac)]-Leu-Arg-Pro-Gly-NH$_2$ 28, pGlu-His-Trp-Ser-Tyr-D-Lys[(PtCl$_2$)(A$_2$bu)]-Leu-Arg-Pro-Gly-NH$_2$ 29, pGlu-His-Trp-Ser-Tyr-D-Lys[(PtCl$_2$)(A$_2$bu-Eac)]-Leu-Arg-Pro-Gly-NH$_2$.

In all of the above embodiments, the compound may also be prepared as the addition salts of pharmaceutically acceptable organic or inorganic acids. As examples, but not as limitations, the following acids may be mentioned hydrochloride, hydrobromide, sulphate, phosphate, fumarate, gluconate, tannate, maleate, acetate, citrate, benzoate, succinate, alginate, pamoate, malate, ascorbate, tartrate, and the like.

ASSAY PROCEDURES

The compounds of this invention exhibit a surprisingly powerful effect on gonadotropin release by the pituitary, bind to tumor cell membranes and inhibit [$^3$H]thymidine incorporation into DNA.

(a) LHRH inhibiting effect

The ability of compounds to influence LH release in vitro is assayed by using a superfused rat pituitary cell system [S. Vigh and A. V. Schally, Peptides, 5 Suppl. 1, 241–247 (1984)].

This effect of the peptides is assayed as follows: Each peptide is perfused through the cells for 9 min (3-ml perfusate) at 3 nM. Immediately after that, a mixture containing the same concentration of peptide and 3 nM LHRH is administered for 3 min. This was followed by four consecutive infusions of 3 nM LHRH for 3 min (1-ml perfusate) at 30-min intervals (30, 60, 90, 120 min). LH content of the 1-ml fractions collected is determined by RIA.

(b) In vivo antiovulatory activity

This activity of the peptides is determined in 4-day-cycling rats as described [A. Corbin and C. W. Beattie, Endocr. Res. Commun., 2, 1–23 (1975)].

(c) Affinity for peptides to human prostate and breast cancer cell membranes

This is determined by using labelled LHRH and [D-Trp$^6$]LHRH. The assay is carried out similarly to that described by T. Kadar et al., Proc. Natl. Acad. Sci. USA, 85, 890–894 (1988).

(d) Ability of peptides of Formula I to inhibit incorporation of [$^3$H]thymidine into DNA of monolayer cultures the rat mammary tumor cell line MT-4 This is assayed as described [V. K. Sondak et al., Cancer Research, 44, 1725–1728 (1984); F. Holzel et al., J. Cancer Res. Clin. Oncol. 109, 217–226 (1985); M. Albert et al., J. Cancer Res. Clin. Oncol. 109, 210–216 (1985)].

SYNTHESIS OF PEPTIDES

The peptides of the present invention may be synthesized by any techniques that are known to those skilled in the peptide art. A summary of the many techniques so available may be found in M. Bodanszky, Principles of Peptide Synthesis, Springer-Verlag, 1984. The techniques of exclusively solid-phase synthesis are set forth in the textbook J. M. Stewart and J. D. Young, Solid Phase Peptide Synthesis, Pierce Chem Co., Rockford, Ill., 1984 (2nd ed.). Classical solution synthesis is described in detail in the treatise "Methoden der Organische Chimie" (Houben-Weyl), Vol. 15, Synthese von peptiden, Parts I and II, Georg Thieme Verlag, Stuttgart, 1974.

In general, these methods comprise the sequential addition of one or more suitably protected amino acids to a growing peptide chain. Normally, either the amino or the carboxyl group of the first amino acid is protected by a suitable protecting group.

The protected amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting (and any solid support) are removed sequentially or concurrently, to afford the final peptide. By simple modification of this general procedure, it is possible to add more than one amino acid at a time to a growing peptide chain, for example, by coupling (under conditions which do not racemize chiral centers) a protected pentapeptide with a properly protected another pentapeptide to form, after deprotection, a decapeptide.

PREFERRED EMBODIMENT OF SYNTHESIS

A particularly preferred method of preparing compounds of the present invention involves a combination of the solid phase and classical (solution) syntheses.

In this particularly preferred method, the alpha-amino function of the amino acids is protected by an acid sensitive group. Suitable protecting groups are t-butyloxycarbonyl (Boc), benzyloxycarbonyl (Z), t-amyloxycarbonyl and the like, especially Boc.

Particularly preferred side chain protecting groups are, for arginine: p-toluenesulfonyl and nitro, tyrosine: benzyl and 2,6-dichlorobenzyl, serine: benzyl, lysine and ornithine: benzyloxycarbonyl or 2-chlorobenzyloxycarbonyl, histidine: p-toluenesulfonyl or 2,4-dinitrophenyl.

The C-terminal amino acid is attached to a suitable solid support. For the synthesis of peptides with free carboxyl group, suitable solid supports are chloromethyl-polystyrene-divinylbenzene polymer, hydroxymethyl-polystyrene-divinylbenzene polymer and the like, especially chloromethyl-polystyrene-1% divinylbenzene polymer. For the synthesis of peptide amides, a useful support is the benzhydrylamino-polystyrene-2% divinyl benzene polymer. Both chloromethyl resins and benzhydrylamine resins are commercially available.

The attachment to the chloromethyl resin is made by means of reaction of the alpha-amino-protected amino acid, especially Boc-amino acids, as its cesium, triethylamine or similar salt in DMF, MeCN or ethanol at elevated temperature. According to another, especially useful approach, Boc-amino acid is attached to the chloromethyl resin in the presence of KF in DMF at about 60° C. for 24 hours with stirring [K. Horiki et al., Chemistry Letters, 1978, 165–168]. The Boc-amino acids is attached to the benzhydrylamine resin by means of a carbodiimide, such as DCC or DIC, or carbodiimide-/HOBt mediated coupling.

The coupling of successive protected amino acids can be carried out in either an automatic or a manual peptide synthesizer as is well known in the art.

The removal of the Boc group may be performed by an acid in a suitable solvent, preferably by 50% trifluoroacetic acid in $CH_2Cl_2$.

Each protected amino acid is preferably introduced in a 2-4 molar, preferably in 3 molar excess, and the coupling is carried out in $CH_2Cl_2$ or $DMF/CH_2Cl_2$ mixtures depending on the solubility of Boc-amino acids at ambient temperature. The coupling agent is normally DIC or other carbodiimide either alone or in the presence of HOBt.

At the end of the solid phase synthesis the fully protected peptide is preferably removed from the resin support by treatment with liquid hydrogen fluoride (HF), which not only cleaves the peptide from the resin but also cleaves all remaining the side chain protecting groups.

The peptides of Formula I wherein $R^6$ is a D-Phe residue carrying the bis-(2-chloroethyl)amino group, i.e. $R^6(Q)$ is a 4-[bis(2-chloroethyl)amino]-D-phenylalanine (D-Mel) residue, are preferably synthesized from fragments (1–5) and (6–10) which are represented by Formulas VII and VIII, respectively:

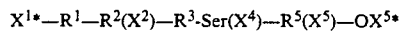

$X^{1*}—R^1—R^2(X^2)—R^3\text{-Ser}(X^4)—R^5(X^5)—OX^{5*}$    VII

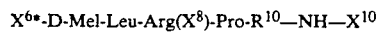

$X^{6*}\text{-D-Mel-Leu-Arg}(X^8)\text{-Pro-}R^{10}—NH—X^{10}$    VIII wherein $R^1$, $R^2$, $R^3$, $R^5$, and $R^{10}$ are as defined hereinabove, $X^{1*}$ is hydrogen, an acyl group of 2–5 carbon atom or carbamyl, $X^2$ is nil or a suitable protecting group for the His imidazole nitrogen, such as Tos or 2,4-dinitrophenyl. The preferred protecting group is Tos.

$X^4$ is hydrogen or a suitable protecting group for the hydroxyl group of Ser such as Bzl or DCB. The preferred protecting group is Bzl.

$X^5$ is hydrogen or a suitable protecting group for the phenolic hydroxyl group of Tyr; DCB is the preferred group; or $X^8$.

$X^{5*}$ is hydrogen or benzyl group being incorporated into a solid support.

$X^{6*}$ is hydrogen or Boc.

$X^8$ is hydrogen or a suitable protecting group for the guanidino group of Arg such as Tos or nitro. The preferred protecting group is Tos.

$X^{10}$ is hydrogen or benzhydryl group being incorporated into a solid support.

Pentapeptide fragment VII and the (6–10) tetrapeptide portion of fragment VIII are preferably prepared by the solid phase method.

Synthesis of fragment VII is commenced with the attachment of protected Arg or Tyr to a chloromethyl resin by using KF in DMF.

The tetrapeptide amide portion of VIII is built up on a benzhydrylamine resin. The free tetrapeptide amide is then coupled with Boc-D-Mel to yield, after deprotection, the free pentapeptide amides.

The ensuing free pentapeptides of Formulas VII and VIII wherein $X^2$, $X^4$, $X^5$, $X^{5*}$, $X^{6*}$, $X^8$, and $X^{10}$ are hydrogen, are condensed by the DCC/HOBt method to afford, after purification by HPLC, the desired peptides of Formula I wherein D-Mel is found at the sixth position.

The peptides of Formula I wherein $R^6$ is $R^{*6}$, that is D-Lys, D-Orn or D-Phe($NH_2$) are preferably prepared from intermediate peptides of Formula V:

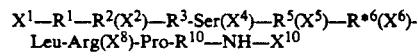

$X^1—R^1—R^2(X^2)—R^3\text{-Ser}(X^4)—R^5(X^5)—R^{*6}(X^6)\text{-}$
$\text{Leu-Arg}(X^8)\text{-Pro-}R^{10}—NH—X^{10}$    V wherein $R^1$, $R^2$, $R^3$, $R^5$, $R^{*6}$, $R^{10}$, $X^1$, $X^2$, $X^4$, $X^5$, $X^8$, and $X^{10}$ are as defined hereinabove, $X^6$ is a suitable protecting group for side chain amino group of Lys, Orn or D-Phe($NH_2$) such as Z, Z(2-Cl); Z(2-Cl) is the preferred protecting group.

The solid phase synthesis of the peptides of Formula V is commenced by the attachment of Boc-protected Gly or D-Ala to a benzhydrylamine resin in $CH_2Cl_2$. The coupling is carried out using DIC. After the removal of the Boc group, the coupling of successive protected amino acids (each is applied in a 3 molar excess) is carried out in $CH_2Cl_2$ or in mixtures of $DMF/CH_2Cl_2$ depending on the solubility of Boc-amino acids. The success of coupling reaction at each stage of the synthesis is preferably monitored by the ninhydrin test as described by Kaiser et al. [Anal. Biochem. 34, 595 (1970)].

After the desired amino acid sequence of intermediate peptides of Formula V has been completed, if desired, the N-terminal acetylation is carried out using $Ac_2O$/imidazole, and the peptide-resin is then treated with liquid HF in the presence of anisole to yield the peptides of Formula V wherein $X^2$, $X^4$, $X^5$, $X^6$, $X^8$, and $X^{10}$ are hydrogen.

The ensuing unprotected intermediate peptides of Formula V are then acylated with Boc-protected A diamino acids to obtain, after deprotection, intermediate peptides of Formula VI:

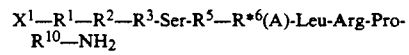

$X^1—R^1—R^2—R^3\text{-Ser-}R^5—R^{*6}(A)\text{-Leu-Arg-Pro-}$
$R^{10}—NH_2$    VI wherein $X^1$, $R^1$, $R^2$, $R^3$, $R^5$, $R^{*6}$, and $R^{10}$ are as defined hereinabove, and A is L,D-2,3-diaminopropyl, L,D-2,4-diaminobutyryl, L,D-2,3-diamonopropyl-6-aminocaproyl or L,D-2,4-diaminobutyryl-6-aminocaproyl.

In an alternate synthesis of intermediate peptides of Formula VI are obtained by deprotection of intermediate peptides of Formula VIA which are prepared by the solid phase method as intermediate peptides having the Formula V, but a suitably protected $R^{*6}(A)$ residue, preferably Boc-$R^{*6}[A(Z)_2]$, incorporated in position 6.

Intermediate peptides of Formula VI are converted into peptides of Formula I wherein residue $R^6$ is $R^{*6}$ and it carries $[(PtCl_2)(A)]$ as the cytotoxic moiety by reacting the peptide with an equivalent amount of $K_2PtCl_4$ in 60–80% aqueous DMF at ambient temperature followed by purification by HPLC. The $PtCl_2$-containing compounds, if desired, can be converted into their $PtY_2$-containing congeners by known procedures.

Peptides of Formula I wherein residue $R^6$ is $R^{*6}$ and carry [(Q")(B)$_2$(A)] as cytotoxic moiety containing non-platinum-group metal ion are obtained from intermediate peptides of Formula VI by reacting with a suitable hydroxy (or carboxy) oxo-compound then a metal salt of pharmaceutically acceptable acid, preferably the acetate of $Cu^{++}$, $Ni^{++}$, $Co^{++}$, $Zn^{++}$ or, for example, $Cd^{++}$, or with a complex formed by the above-mentioned hydroxy (or carboxy) oxo-compound and the metal itself, in 60–80% aqueous DMF solution the desired peptide-metal-complex is then isolated, preferably by HPLC.

All of the peptides are considered to release gonadotrophin from the pituitary in mammals at very low dosages.

The peptides of the invention are often administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzonate, succinate, alginate, pamoate, malate, ascorbate, tartrate, and the like. If the active ingredient is to be administered in tablet form, the tablet may contain a pharmaceutically acceptable diluent which includes a binder, such as tragacanth, corn starch or gelatin; a disintegrating agent, such as alginic acid and a lubricant, such as magnesium stearate.

If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of LHRH.

These peptides can be administered to mammals intravenously, subcutaneously, intramuscularly, orally, intranasally or intravaginally to achieve fertility inhibition and/or control and also in applications calling for reversible suppression of gonadal activity, such as for the management of precocious puberty or during radiation- or chemo-therapy. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications obvious to one having the ordinary skill in this art may be made without departing from the scope of the invention, which is set forth in the claims which are appended thereto. Substitutions known in the art which do not significantly detract from its effectiveness may be employed in the invention.

PREPARATION I

Boc-D-Mel-OPCP

D-4-[bis-(2-chloroethyl)amino]phenylalanine, D-Mel, (5 mmol) was converted to its Boc derivative as described for the L isomer [H. Kun-hwa and G. R. Marshall, J. Med. Chem. 24, 1304–1310 (1981)] with the exception that di-tert-butyl dicarbonate was used as acylating agent instead of Boc-azide. The oily product, Boc-D-Mel, was dissolved in DMF (5 ml) and cooled to 0° C. To the stirred solution triethylamine (5 mmol) and pentachlorohenyl trichloro- acetate [M. Fujino and C. Hatanaka, Chem. Pharm. Bull., 16, 929 (1968)](5 mmol) were added. After 10-min. stirring, the reaction mixture was diluted with ice-water, and the crystalline material separated was filtered off, washed with ice water and ethanol and, after drying, washed with MeCN and dried again. Boc-D-Mel-OPCP thus obtained (about 3 mmol) has a m.p. of 138°–140° C.

PREPARATION II pGlu-His-Trp-Ser-Tyr

Boc-Tyr(DCB)-OH (1.5 mmol) dissolved in DMF (10 ml) was reacted with a chloromethyl-polystyrene-1% divinyl-benzene resin (Bachem, Torrance, Calif.) (1 g) and KF (3 mmol) with stirring at 60° for 24 hours. The ensuing Boc-Tyr-O-RESIN (taken as 1 mmol) was coupled sequentially with a 3 molar excess of protected amino acids in accordance with the synthesis program, as follows:

| STEP | REAGENTS AND OPERATIONS | MIXING TIMES (min.) |
|------|------------------------|---------------------|
| 1    | Deprotection: 50% TFA in DCM (twice) | 5 and 25 |
| 2    | DCM wash | 2 |
| 3    | 2-Propanol wash | 1 |
| 4    | Neutralization: 10% TEA in DCM | 2 |
| 5    | MeOH wash | 1 |
| 6    | Neutralization: 10% TEA in DCM | 2 |
| 7    | MeOH wash | 1 |
| 8    | DCM wash (three times) | 2 |
| 9    | Coupling: Boc-amino acid in DCM or DMF depending on the solubility of the particular protected amino acid, plus DIC | 60–90 |
| 10   | MeOH (or DMF then MeOH) wash | 2 |
| 11   | DCM wash | 2 |
| 12   | MeOH wash | 2 |
| 13   | DCM wash (three times) | 2 |

Steps 1–13 complete a coupling cycle for one amino acid. Thus, the resin was treated during successive coupling cycles with Boc-Ser(Bzl), Boc-Trp, Boc-His(Tos), and pGlu (3 mmol of each).

The peptide resin obtained (2.1 g) was treated with 2 ml anisole and 20 ml HF at 0° C. for 45 min. After elimination of HF under high vacuum, the peptide-resin remainder was washed with dry diethyl ether and ethyl acetate. The peptide was then extracted with 50% aqueous acetic acid, separated from the resin by filtration, and lyophilized.

Crude peptide (686 mg) was purified using a Beckman Prep-350 preparative HPLC system [with a Beckman Type 163 variable wavelength UV detector]. Separations were achieved on a 41.5×250 mm DYNAMAX column packed with spherical C18 silica gel (300 A pore size, 12 m particle size) (RAININ Inc. Co. Woburn, Mass.) with solvents A: 0.1% aqueous TFA and B: is 0.1% TFA in 70% aqueous MeCN (referred to as system i in the following) using a gradient of 15–30% B in 30 min. The column eluate was monitored at 220 nm and 280 nm.

The peptide thus obtained (350 mg) was judged to be substantially (>95%) pure by using a Hewlett-Packard Model HP-1090 liquid chromatograph. The peptides were chromatographed on a 4.6×250 mm W-Porex 5 m C18 column (Phenomenex, Rancho Palos Verdes, Calif.) at a flow rate of 1.2 ml/min. with solvent system i in a linear gradient mode (15–45% B in 60 min). Retention time for the pentapeptide was 12.4 min.

The preparation of peptide Ac-Pro-D-Phe(4Cl)-D-Trp-Ser-Tyr is accomplished as described in above with the exception that Boc-D-Trp, Boc-D-Phe(4Cl) and Boc-Pro are incorporated in place of Boc-Trp, Boc-His(Tos) and Boc-D-Nal(2), respectively. The peptide thus obtained as an HPLC retention time of 20.3 min when using system i in a linear gradient mode (30–60% B in 30 min).

PREPARATION III

Ac-D-Nal(2)-D-Phe(4Cl)-D-Pal(3)-Ser-Arg (IIIA) and
Ac-D-Nal(2)-D-Phe(4Cl)-D-Trp-Ser-Arg (IIIB)

Boc-Arg(Tos) (1.5 mmol) was linked to a chloromethyl-polystyrene-1% divinylbenzene resin (Bachem, Torrance, Calif.) (1 g) by means of KF (3 mmol) in DMF (10 ml) while stirring at 60° C. for 24 hours. Boc-Arg(Tos)-O-RESIN thus obtained (taken as 1 mmol) was coupled sequentially with a 3 molar excess of protected amino acids in accordance with the synthesis program given in Preparation II. The amino acid derivatives used during successive coupling cycles were: Boc-Ser(Bzl), Boc-D-Pal(3), Boc-D-Phe(4Cl), and Boc-D-Nal(2). After the amino acid sequence of the pentapeptides has been completed, the terminal Boc group was removed and the N-terminal acetylated by using 10-fold excess of Ac2O/imidazole to yield peptide resin Ac-D-Nal(2)-D-Phe(4Cl)-D-Pal(3)-Ser(Bzl)-Arg(Tos)-O-RESIN.

Proceeding in a similar manner, but incorporating Boc-D-Trp in place of Boc-D-Pal(3) in position 3, there is prepared peptide resin Ac-D-Nal(2)-D-Phe(4Cl)-D-Trp-Ser(Bzl)-Arg(Tos)-O-RESIN.

Peptide-resins were treated with HF as described in Preparation II. The crude products were purified by HPLC with gradient elution (30–60% B in 60 min.). Purified pentapeptides IIIA and IIIB have retention times of 11.8 min. and 25.5 min., respectively, when using solvent system i in a linear gradient mode (30–60% B in 30 min).

The preparation of peptide Ac-Pro-D-Phe(4Cl)-D-Trp-Ser-Arg is accomplished as described above with the exception that Boc-D-Trp and Boc-Pro are incorporated in place of Boc-D-Pal(3) and Boc-D-Nal(2), respectively. The peptide thus obtained as an HPLC retention time of 13.5 min when using system i in a linear gradient mode (30–60% B in 30 min).

PREPARATION IV

H-D-Mel-Leu-Arg-Pro-Gly-NH2 (IVA) and
H-D-Mel-Leu-Arg-Pro-D-Ala-NH2 (IVB)

The C-terminal tetrapeptide amide portions of IVA and IVB were built step by step on a benzhydrylamine HCl resin containing about 1 meq NH2/g (Advanced ChemTech, Louisville, Ky.) in a reaction vessel for manual solid-phase synthesis starting with Boc-Gly and Boc-D-Ala, respectively, in accordance with the procedures set forth below.

The benzhydrylamine HCl resin (1 g, about 1 mmol), after neutralization with 10% TEA in CH2Cl2, was coupled sequentially with 3 molar excess of protected amino acids in accordance with the Schedule as follows:

| STEP | REAGENTS AND OPERATIONS | MIXING TIMES (min) |
|---|---|---|
| 1 | Coupling: Boc-amino acid in DCM or DMF depending on the solubility of the particular protected amino acid, plus DIC | 60–90 |
| 2 | MeOH (or DMF then MeOH) wash | 2 |
| 3 | DCM wash | 2 |
| 4 | MeOH wash | 2 |
| 5 | DCM wash (three times) | 2 |
| 6 | Deprotection: 50% TFA in DCM (twice) | 5 and 25 |
| 7 | DCM wash | 2 |
| 8 | 2-Propanol wash | 1 |
| 9 | Neutralization: 10% TEA in DCM | 2 |
| 10 | MeOH wash | 1 |
| 11 | Neutralization: 10% TEA in DCM | 2 |
| 12 | MeOH wash | 1 |
| 13 | DCM wash (three times) | 2 |

Thus, the resin was treated with Boc-Gly, Boc-Pro, Boc-Arg(Tos), and Boc-Leu during successive coupling cycles to yield peptide-resin with structure of Boc-Leu-Arg(Tos)-Pro-Gly-NH-RESIN. Similarly, reacting the resin with Boc-D-Ala, Boc-Pro, Boc-Arg(Tos), and Boc-Leu during successive coupling cycles leads to the peptide resin having the structure of Boc-Leu-Arg(Tos)-Pro-D-Ala-NH-RESIN.

The peptide-resins thus obtained were treated with anisole and HF as described in Preparation II. The free peptide amides were extracted with DMF, separated from the resin by filtration, evaporated, and the residue was triturated with MeCN to yield free tetrapeptide amides H-Leu-Arg-Pro-Gly-NH2.2 HF (390 mg) and H-Leu-Arg-Pro-D-Ala-NH2.2 HF (400 mg), respectively.

To a stirred solution of H-Leu-Arg-Pro-Gly-NH2.2 HF (240 mg) in DMF (1 ml) cooled to 0° C., DIEA (0.18 ml) and Boc-D-Mel-OPCP (Preparation I, 330 mg) were added. Stirring was continued until dissolution of the activated ester, than the reaction mixture was kept at 0° C. overnight. After evaporation under vacuum, the residue was first triturated with diethyl ether then dissolved in 50% aqueous MeCN and subjected to purification by HPLC with solvents A: 0.2% AcOH and B: 0.2% AcOH in 70% aqueous MeCN (referred to as system ii in the following) using a gradient of 30–60% B in 60 min. The pure Boc-protected pentapeptide thus obtained was treated with 10% HCl in ethyl acetate for 30 min. to yield the HCl salt of H-D-Mel-Leu-Arg-Pro-Gly-NH2, IVA (250 mg).

Proceeding in a similar manner but using tetrapeptide amide H-Leu-Arg-Pro-D-Ala-NH2.2 HF (250 mg) as amino component, there was prepared the HCl salt of H-D-Mel-Leu-Arg-Pro-D-Ala-NH2, IVB (245 mg). HPLC retention times for peptides IVA and IVB were 15.8 min. and 19.4 min., respectively, when using solvent system i in a linear gradient mode (30–60% B in 30 min).

PREPARATION V pGlu-His-Trp-Ser-Tyr-D-Lys(DL-A$_2$pr)-Leu-Arg-Pro-Gly-NH$_2$ (VA)

pGlu-His-Trp-Ser-Tyr-D-Lys(DL-A$_2$bu)-Leu-Arg-Pro-Gly-NH$_2$ (VB)

To a solution of [D-Lys$^6$]LHRH [N. C. Nicholas et al., J. Med. Chem., 19, 937–941 (1976)] (323 mg of the TFA salt) in DMF (1 ml) cooled to 0° C., Boc$_2$-DL-A$_2$pr (66 mg), HODNP (89 mg), TEA (0.14 ml), and 0.04 ml DIC were added then allowed to stand at 0° C. overnight. Reaction mixture was concentrated under vacuum, the oily residue was dissolved in 0.1% TFA and diethyl ether and the aqueous phase was subjected to HPLC in solvent system i in a linear gradient mode (20–50% solvent B in 60 min). The pure Boc-protected peptide was then treated with 10% HCl in ethyl acetate to yield the HCl salt of [D-Lys(DL-A$_2$pr)$^6$]LHRH (VA) (246 mg).

Proceeding in a similar manner but using Boc$_2$-DL-A$_2$bu (70 mg) as acid-component, there was prepared the HCl salt of [D-Lys(DL-A$_2$bu)$^6$]LHRH (VB) (230 mg). HPLC retention times for peptides VA and VB were 12.3 min. and 12.1 min., respectively, when using solvent system i in a linear gradient mode (15–45% B in 30 min).

PREPARATION VI pGlu-His-Trp-Ser-Tyr-D-Lys(A$_2$pr)-Leu-Arg-Pro-Gly-NH$_2$ (VIA)

pGlu-His-Trp-Ser-Tyr-D-Lys(A$_2$bu)-Leu-Arg-Pro-Gly-NH$_2$ (VIB)

The syntheses of peptides VIA and VIB are accomplished as described in Procedure V with the exception that Boc$_2$-A$_2$pr and Boc$_2$-A$_2$bu are used as acylating components in place of Boc$_2$-DL-A$_2$pr and Boc$_2$-DL-A$_2$bu, respectively.

PREPARATION VII

Ac-D-Phe(4Cl)-D-Phe(4Cl)-D-Trp-Ser-Tyr-D-Lys(DL-A$_2$pr)-Leu-Arg-Pro-D-Ala-NH$_2$ (VIIA) and Ac-D-Phe(4Cl)-D-Phe(4Cl)-D-Trp-Ser-Tyr-D-Lys(DL-A$_2$bu)-Leu-Arg-Pro-D-Ala-NH$_2$ (VIIB)

Preparation of VIIA and VIIB were accomplished as described in Preparation VA and VB, respectively, with the exception that [Ac-D-Phe(4Cl)$^1$,D-Phe(4Cl)$^2$,D-Trp$^3$,D-Lys$^6$,D-Ala$^{10}$]LHRH [H. D. Coy et al., Endocrinology, 110, 1445–1447 (1982)] (330 mg) was used as amino-component in place of [D-Lys$^6$]LHRH to yield the desired intermediate peptides as HCl salts. The intermediate peptides VIIA and VIIB have HPLC retention times of 20.7 min. and 20.6 min., respectively, when using solvent system i in a linear gradient mode (30–60% B in 30 min).

PREPARATION VIII

Ac-D-Nal(2)-D-Phe(4Cl)-D-Pal(3)-Ser-Arg-D-Lys(DL-A$_2$pr)-Leu-Arg-Pro-D-Ala-NH$_2$ (VIIIA)

Ac-Nal(2)-D-Phe(4Cl)-D-Trp-Ser-Arg-D-Lys(DL-A$_2$pr)-Leu-Arg-Pro-D-Ala-NH$_2$ (VIIIB) and Ac-Nal(2)-D-Phe(4Cl)-D-Pal(3)-Ser-Arg-D-Orn(DL-A$_2$pr)-Leu-Arg-Pro-D-Ala-NH$_2$ (VIIIC)

The syntheses of VIIIA, VIIIB and VIIIC were commenced with the preparation of the linear decapeptide precursors containing D-Lys or D-Orn residue at position 6. These precursor peptides were prepared by the solid-phase technique on a benzhydrylamine HCl resin in accordance with the procedures set forth in the Schedule of Preparation IV.

Thus, the resin (0.5 g containing about 0.5 mmole NH$_2$) was treated during the ten successive coupling cycles with Boc-D-Ala, Boc-Pro, Boc-Leu, Boc-Arg(Tos), Boc-Lys[Z(2-Cl)], Boc-Arg(Tos), Boc-Ser(Bzl), Boc-D-Pal(3), Boc-D-Phe(4Cl), Boc-D-Nal(2) and finally with Ac$_2$O/imidazole to yield a peptide-resin which was then treated with HF and anisole to afford the free, D-Lys-containing decapeptide precursor of VIIIA:

Ac-D-Nal(2)-D-Phe(4Cl)-D-Pal(3)-Ser-Arg-D-Lys-Leu-Arg-Pro-D-Ala-NH$_2$ (540 mg of the TFA salt).

Proceeding in a similar manner but incorporating Boc-D-Trp in place of Boc-D-Pal(3) at position 3, there was prepared the free, D-Lys-containing decapeptide precursor of VIIIB:

Ac-D-Nal(2)-D-Phe(4Cl)-D-Trp-Ser-Arg-D-Lys-Leu-Arg-Pro-D-Ala-NH$_2$ (500 mg of the TFA salt).

Again proceeding as above but introducing Boc-D-Orn(Z) in place of Boc-D-Lys[Z(2-Cl)] at position 6, there was prepared the free, D-Orn-containing decapeptide precursor of VIIIC:

Ac-D-Nal(2)-D-Phe(4Cl)-D-Pal(3)-Ser-Arg-D-Orn-Leu-Arg-Pro-D-Ala-NH$_2$ (520 mg of the TFA salt).

The decapeptide precursors were acylated with Boc$_2$-DL-A$_2$pr and the Boc-protected undecapeptides obtained were deprotected as described in Preparation V to give the HCl salt of intermediate peptides VIIIA, VIIIB, and VIIIC. HPLC retention times of peptides VIIIA, VIIIB and VIIIC were 10.7 min, 17.7 min and 11.0 min, respectively, when using solvent system i in a linear gradient mode (30–60% B in 30 min).

PREPARATION IX

Boc$_2$-DL-A$_2$bu-Eac (IXA), Boc$_2$-A$_2$bu-Eac (IXB)

Boc$_2$-DL-A$_2$pr-Eac (IXC) and Boc$_2$-A$_2$pr-Eac (IXD)

To a mixed anhydride prepared from Boc$_2$-DL-A$_2$bu (0.64 g) and ethyl chloroformate (0.2 ml) in the presence of TEA (0.28 ml) in DMF solution (4 ml), %-aminocaproic acid methyl ester hydrochloride (0.4 g) and TEA (0.31 ml) in chloroform (4 ml) were added with stirring at −10° C. Stirring was continued for 2 hours at 0° C.–5° C. then the reaction mixture was concentrated to about 5 ml under reduced pressure. The residue was dissolved in water and ethyl acetate, the organic layer was successively washed with 1M KHSO$_4$, water, and a saturated NaHCO$_3$ solution, then dried over Na$_2$SO$_4$ and evaporated. The ensuing dipeptide methyl ester, Boc$_2$-DL-A$_2$bu-Eac-OMe, was dissolved in methanol (5 ml) and 1M sodium hydroxide (3 ml). After one hour, the mixture was acidified with 1M KHSO$_4$ (3 ml) and extracted with ethyl acetate. The ethyl acetate solution was washed with water, dried over Na$_2$SO$_4$, and evaporated to yield Boc$_2$-DL-A$_2$bu-Eac (IXA) (0.8 g).

Proceeding in a similar manner but using Boc$_2$-A$_2$bu (0.64 g), Boc$_2$-DL-A$_2$pr (0.61 g) and Boc$_2$-A$_2$pr (0.61 g) as acid component, there are prepared Boc$_2$-A$_2$bu-Eac (IXB), Boc$_2$-DL-A$_2$pr-Eac (IXC) and Boc$_2$-A$_2$pr-Eac (IXD), respectively.

PREPARATION X pGlu-His-Trp-Ser-Tyr-D-Lys(DL-$A_2$pr-Eac)-Leu-Arg-Pro-Gly-$NH_2$ (XA)

pGlu-His-Trp-Ser-Tyr-D-Lys(DL-$A_2$bu-Eac)-Leu-Arg-Pro-Gly-$NH_2$ (XB)

The synthesis of XA and XB was accomplished as described in Preparation V with the exception that $Boc_2$-DL-$A_2$pr-Eac (Preparation IXC) (90 mg) and $Boc_2$-DL-$A_2$bu-Eac (Preparation IXA) (95 mg) were used in place of $Boc_2$-DL-$A_2$pr and $Boc_2$-DL-$A_2$bu, respectively. After purification by HPLC and deblocking with HCl in ethyl acetate, the desired products, [D-Lys(DL-$A_2$pr-Eac)$^6$]LHRH (260 mg) and [D-Lys(DL-$A_2$bu-Eac)$^6$]LHRH (260 mg), have HPLC retention times of 14.2 min and 14.4 min, respectively.

PREPARATION XI

Boc-D-Lys($Z_2$-$A_2$pr) (XIA) and Boc-D-Lys($Z_2$-$A_2$bu) (XIB)

To a mixed anhydride prepared from $Z_2$-$A_2$pr (0.72 g) and ethyl chloroformate (0.2 ml) in the presence of TEA (0.28 ml) in DMF solution (4 ml), Boc-D-Lys (0.5 g) and (0.3 ml) TEA in 50% aqueous DMF (4 ml) were added with stirring at 0° C. After 2 hours stirring at 0° C., the reaction mixture was concentrated to an oil under reduced pressure, dissolved in water and ethyl acetate, acidified with 1M $KHSO_4$. The organic phase was washed with water, then dried over $Na_2SO_4$ and evaporated under vacuum to yield Boc-D-Lys($Z_2$-$A_2$pr) (XIA) (1.1 g).

Proceeding in a similar manner but using $Z_2$-$A_2$bu (0.76 g) as acid component, there was prepared Boc-D-Lys($Z_2$-$A_2$bu) (1.1 g) (XIB).

PREPARATION XII pGlu-His-Trp-Ser-Tyr-D-Lys($A_2$pr)-Leu-Arg-Pro-Gly-$NH_2$ (VIA)

pGlu-His-Trp-Ser-Tyr-D-Lys($A_2$bu)-Leu-Arg-Pro-Gly-$NH_2$ (VIB)

In this Procedure compounds VIA and VIB were built step by step on a benzhydrylamine HCl resin containing about 1 meq $NH_2$/g (Advanced ChemTech, Louisville, Ky.) in a reaction vessel for manual solid-phase synthesis starting with Boc-Gly in accordance with the procedures set forth below.

The benzhydrylamine HCl resin (1 g, about 1 mmol), after neutralization with 10% TEA in $CH_2Cl_2$, was coupled sequentially with 3 molar excess of protected amino acids in accordance with the Schedule given in Procedure IV. Thus, the resin was treated with Boc-Gly, Boc-Pro, Boc-Arg(Tos), Boc-Leu, Boc-D-Lys($Z_2$-$A_2$pr) (Preparation XIA), Boc-Tyr(DCB), Boc-Ser(Bzl), Boc-His(Z), and pGlu during successive coupling cycles to yield peptide-resin with structure of pGlu-His(Tos)-Trp-Ser(Bzl)-Tyr(DCB)-D-Lys($Z_2$-$A_2$pr)-Leu-Arg(Tos)-Pro-Gly-NH-RESIN.

Proceeding in a similar manner, but reacting the resin with Boc-Gly, Boc-Pro, Boc-Arg(Tos), Boc-Leu, Boc-D-Lys($Z_2$-$A_2$bu) (Preparation XIB), Boc-Tyr(DCB), Boc-Ser(Bzl), Boc-His(Tos), and pGlu during successive coupling cycles leads to the peptide resin having the structure of pGlu-His(Tos)-Trp-Ser(Bzl)-Tyr(DCB)-D-Lys($Z_2$-$A_2$bu)-Leu-Arg(Tos)-Pro-Gly-NH-RESIN.

The peptide-resins thus obtained were treated with anisole and HF, and the crude free peptides were isolated as described in Preparation II. Thereafter the crude peptides (1.2–1.4 g) were subjected to purification by HPLC as described in Preparation II.

Peptides VIA and VIB thus obtained (0.7–0.8 g) were judged to be substantially (>95%) pure. HPLC retention times for peptides VIA and VIB were 12.4 min and 12.2 min, respectively, when using solvent system i in a linear gradient mode (15–45% B in 30 min).

PREPARATION XIII

Ac-D-Nal(2)-D-Phe(4Cl)-D-Pal(3)-Ser-Arg-D-Lys-($A_2$pr)-Leu-Arg-Pro-D-Ala-$NH_2$ (XIIIA) and Ac-D-Nal(2)-D-Phe(4Cl)-D-Pal(3)-Ser-Arg-D-Lys($A_2$bu)-Leu-Arg-Pro-D-Ala-$NH_2$ (XIIIB)

Compounds XIIIA and XIIIB were built step by step on a benzhydrylamine HCl resin containing about 1 meq $NH_2$/g (Advanced ChemTech, Louisville, Ky.) in a reaction vessel for manual solid-phase synthesis starting with Boc-D-Ala in accordance with the procedures set forth below.

The benzhydrylamine HCl resin (1 g, about 1 mmol), after neutralization with 10% TEA in $CH_2Cl_2$, was coupled sequentially with 3 molar excess of protected amino acids in accordance with the Schedule given in Procedure IV. Thus, the resin was treated with Boc-D-Ala, Boc-Pro, Boc-Arg(Tos), Boc-Leu, Boc-D-Lys($Z_2$-$A_2$pr) (Preparation XIA), Boc-Arg(Tos), Boc-Ser(Bzl), Boc-D-Pal(3), Boc-D-Phe(4Cl), and Boc-D-Nal(2). After the amino acid sequence of the decapeptide has been completed, the terminal Boc group was removed and the N-terminal was acetylated by using 10-fold excess of $Ac_2O$ and imidazole to yield peptide-resin with structure of Ac-D-Nal(2)-D-Phe(4Cl)-D-Pal(3)-Ser(Bzl)-Arg(Tos)-D-Lys($Z_2$-$A_2$pr)-Leu-Arg(Tos)-Pro-D-Ala-NH-RESIN.

Proceeding in a similar manner, but reacting the resin with Boc-D-Ala, Boc-Pro, Boc-Arg(Tos), Boc-Leu, Boc-D-Lys($Z_2$-$A_2$bu) (Preparation XIB), Boc-Arg(Tos), Boc-Ser(Bzl), Boc-D-Pal(3), Boc-D-Nal(2), and $Ac_2O$/imidazole during successive coupling cycles leads to the peptide resin having the structure of Ac-D-Nal(2)-D-Phe(4Cl)-D-Pal(3)-Ser(Bzl)-Arg(Tos)-D-Lys($Z_2$-$A_2$bu)-Leu-Arg(Tos)-Pro-D-Ala-NH-RESIN.

The peptide-resins thus obtained were treated with anisole and HF, and the crude free peptides were isolated as described in Preparation II. Thereafter the crude peptides (1.3–1.4 g) were subjected to purification by HPLC using solvent system i in a linear gradient mode (20–50% B in 60 min). Peptides XIIIA and XIIIB thus obtained (0.7–0.8 g) were judged to be substantially (>95%) pure. HPLC retention times for peptides XIIIA and XIIIB were 10.8 min and 10.6 min, respectively, when using solvent system i in a linear gradient mode (30–60% B in 30 min).

PREPARATION XIV

Ac-D-Nal(2)-D-Phe(4Cl)-D-Trp-Ser-Arg-D-Lys-($A_2$pr)-Leu-Arg-Pro-D-Ala-$NH_2$ (XIVA) and Ac-D-Nal(2)-D-Phe(4Cl)-D-Trp-Ser-Arg-D-Lys($A_2$bu)-Leu-Arg-Pro-D-Ala-$NH_2$ (XIVB)

The synthesis of XIVA and XIVB was accomplished as described in Preparation XIII for the synthesis of XIIIA and XIIIB with the exception that Boc-D-Trp was incorporated in place of Boc-D-Pal(3) in position 3.

HPLC retention times of XIVA and XIVB were 17.5 min and 17.7 min, respectively when using solvent system i in a linear gradient mode (30–60% B in 30 min).

PREPARATION XV

Ac-D-Nal(2)-D-Phe(4Cl)-D-Pal(3)-Ser-Arg-D-Lys-($A_2$pr-Eac)-Leu-Arg-Pro-D-Ala-$NH_2$ (XVA)

Ac-Nal(2)-D-Phe(4Cl)-D-Trp-Ser-Arg-D-Lys($A_2$bu-Eac)-Leu-Arg-Pro-D-Ala-$NH_2$ (XVB)

The synthesis of XVA and XVB was accomplished as described in Preparation VIII with the exception that $Boc_2$-$A_2$pr-Eac (Preparation IXD) (90 mg) and $Boc_2$-$A_2$bu-Eac (Preparation IXB) (95 mg) were used in place of $Boc_2$-DL-$A_2$pr and $Boc_2$-DL-$A_2$bu, respectively. After purification by HPLC and deblocking with HCl in ethyl acetate, the desired products, XVA (226 mg) and XVB (247 mg), have HPLC retention times of 11.4 min and 11.7 min, respectively using solvent system i in a linear gradient mode (30–60% B in 30 min).

EXAMPLE I

The synthesis of peptide pGlu-His-Trp-Ser-Tyr-D-Mel-Leu-Arg-Pro-Gly-$NH_2$ was accomplished by coupling of pentapeptides pGlu-His-Trp-Ser-Tyr-OH (Preparation II, 70 mg) and H-D-Mel-Leu-Arg-Pro-Gly-$NH_2$ (Preparation IVA, 85 mg of the HCl salt) in DMF (0.2 ml containing 0.02 ml DIEA) by means of DCC (30 mg) in the presence of HOBt (20 mg) at 0° C. for 24 hours. The reaction mixture was concentrated under vacuum. The crude material thus obtained is purified on a Beckman HPLC system (Typ 142) using a DYNAMAX Macro 21.2×250 mm column (300 A° pore size, 12 m particle size) with solvent system i in a linear gradient mode (30–60% B in 60 min) to isolate the desired [D-$Mel^6$]LHRH (65 mg) with a HPLC retention time of 11.4 min when using solvent system i in a linear gradient mode (40–80% B in 40 min).

EXAMPLE II

The synthesis of peptide Ac-D-Nal(2)-D-Phe(4Cl)-D-Pal(3)-Ser-Arg-D-Mel-Leu-Arg-Pro-D-Ala-$NH_2$ was accomplished by coupling of pentapeptides Ac-D-Nal(2)-D-Phe(4 Cl)-D-Pal(3)-Ser-Arg-OH (Preparation IIIA, 85 mg) and H-D-Mel-Leu-Arg-Pro-D-Ala-$NH_2$ (Preparation IV, 85 mg) in DMF solution as described in Example I. The reaction mixture was subjected to HPLC using solvent system ii in a linear gradient mode (30–60% B in 60 min) to afford the desired [Ac-D-$Nal(2)^1$, D-$Phe(4Cl)^2$,D-$Pal(3)^3$,$Arg^5$,D-$Mel^6$,D-$Ala^{10}$]LHRH (60 mg) with a HPLC retention time of 19.2 min when using solvent system i in a linear gradient mode (40–80% B 40 min).

The synthesis of peptide Ac-Pro-D-Phe(4Cl)-D-Trp-Ser-Tyr-D-Mel-Leu-Arg-Pro-Gly-$NH_2$ is accomplished by coupling of pentapeptides Ac-Pro-D-Phe(4Cl)-D-Trp-Ser-Tyr-OH (Preparation II, 80 mg) and H-D-Mel-Leu-Arg-Pro-Gly-$NH_2$ (Preparation IV, 80 mg) in DMF solution as described in Example I. The reaction mixture is subjected to HPLC using solvent system ii in a linear gradient mode (20–50% B in 60 min) to afford the desired [Ac-$Pro^1$,D-$Phe(4Cl)^2$, D-$Trp^3$, D-$Mel^6$]LHRH (65 mg) with a HPLC retention time of 25.2 min when using solvent system i in a linear gradient mode (40–80% B 40 min).

The synthesis of peptide Ac-Pro-D-Phe(4Cl)-D-Trp-Ser-Arg-D-Mel-Leu-Arg-Pro-Gly-$NH_2$ is accomplished by coupling of pentapeptides Ac-Pro-D-Phe(4Cl)-D-Trp)-Ser-Arg-OH (Preparation III, 80 mg) and H-D-Mel-Leu-Arg-Pro-Gly-$NH_2$ (Preparation IV, 80 mg) in DMF solution as described in Example I. The reaction mixture is subjected to HPLC using solvent system ii in a linear gradient mode (20–50% B in 60 min) to afford the desired [Ac-$Pro^1$,D-$Phe(4Cl)^2$,D-$Trp^3$,$Arg^5$,D-$Mel^6$]LHRH (60 mg) with a HPLC retention time of 20.7 min when using solvent system i in a linear gradient mode (40–80% B 40 min).

The synthesis of peptide Ac-D-Nal(2)-D-Phe(4Cl)-D-Trp-Ser-Arg-D-Mel-Leu-Arg-Pro-D-Ala-$NH_2$ is accomplished by coupling by coupling of pentapeptides Ac-D-Nal(2)-D-Phe(4Cl)-D-Trp-Ser-Arg-OH (Preparation III, 85 mg) and H-D-Mel-Leu-Arg-Pro-D-Ala-$NH_2$ (Preparation IV, 85 mg) in DMF solution as described in Example I. The reaction mixture is subjected to HPLC using solvent system ii in a linear gradient mode (40–70% B in 60 min) to afford the desired [Ac-D-$Nal(2)^1$,D-$Phe(4Cl)^2$,D-$Trp^3$,$Arg^5$,D-$Mel^6$,D-$Ala^{10}$]LHRH (65 mg) with a HPLC retention time of 27.1 min when using solvent system i in a linear gradient mode (40–80% B 40 min).

EXAMPLE III

The peptide pGlu-His-Trp-Ser-Tyr-D-Lys[($PtCl_2$)(DL-$A_2$pr)]-Leu-Arg-Pro-Gly-$NH_2$ was prepared by reacting [D-Lys(DL-$A_2$pr)$^6$]LHRH (Preparation V, 60 mg of the HCl salt) in 0.2 ml DMF with sodium acetate (10 mg) and potassium chloroplatinate (18 mg) dissolved in 0.2 ml water for 24 hours. Thereafter the reaction mixture was diluted with water and subjected to HPLC as in Example I using solvent system ii in a linear gradient mode (15–55% B in 40 min). The desired Pt-complex [D-Lys[($PtCl_2$)(DL-$A_2$pr)]$^6$]LHRH (45 mg) has HPLC retention time of 10.9 min when using solvent system i in a linear gradient mode (20–60% B in 40 min).

The peptides pGlu-His-Trp-Ser-Tyr-D-Lys[($PtCl_2$)($A_2$bu)]-Leu-Arg-Pro-Gly-$NH_2$ and pGlu-His-Trp-Ser-Tyr-D-Lys[($PtCl_2$)($A_2$bu-Eac)]-Leu-Arg-Pro-Gly-$NH_2$ are prepared as described in Example III with the exception that [D-Lys($A_2$bu)$^6$]LHRH (Preparation VI) and [D-Lys($A_2$bu-Eac)$^6$]LHRH (Preparation XB), respectively, are used in place of [D-$Lys^6$]LHRH as starting material. The ensuing Pt-complexes [D-Lys[($PtCl_2$)($A_2$bu)]$^6$]LHRH and [D-Lys[($PtCl_2$)($A_2$bu-Eac)]$^6$]LHRH have HPLC retention times of 11.6 min and 13.6 min, respectively when using solvent system i in a linear gradient mode (20–60% B in 40 min).

EXAMPLE IV

The synthesis of peptide Ac-D-Phe(4Cl)-D-Phe(4Cl)-D-Trp-Ser-Tyr-D-Lys[($PtCl_2$)(DL-$A_2$pr)]-Leu-Arg-Pro-D-Ala-$NH_2$ was accomplished as described in Example III with the exception that [Ac-D-$Phe(4Cl)^1$,D-$Phe(4Cl)^2$,D-$Trp^3$,D-Lys (DL-$A_2$pr)$^6$,D-$Ala^{10}$]LHRH (Preparation VII, 65 mg of the HCl salt) was used as starting material in place of [D-Lys(DL-$A_2$pr)$^6$]LHRH. The desired peptide-Pt-complex [Ac-D-$Phe(4Cl)^1$,D-$Phe(4Cl)^2$,D-$Trp^3$, D-Lys[($PtCl_2$)(DL-$A_2$pr)]$^6$,D-$Ala^{10}$]LHRH (50 mg) has HPLC retention time of 35.5 min. under conditions given in Example III.

EXAMPLE V

The synthesis of peptide Ac-D-Nal(2)-D-Phe(4Cl)-D-Trp-Ser-Arg-D-Lys[($PtCl_2$)(DL-$A_2$pr)]-Leu-Arg-Pro-D-Ala-$NH_2$ was accomplished as described in Example III with the exception that [Ac-D-$Nal(2)^1$,D-

Phe(4 Cl)$^2$,D-Trp$^3$,Arg$^5$,D-Lys(DL-A$_2$pr)$^6$,D-Ala$^{10}$]LHRH (Preparation VIIIB, 66 mg) was used as starting material in place of [D-Lys(DL-A$_2$pr)$^6$]LHRH. The desired peptide Pt-complex obtained (45 mg) has HPLC retention time of 32.6 min. under conditions given in Example III.

EXAMPLE VI

Peptide pGlu-His-Trp-Ser-Tyr-D-Lys[(Cu++)(SAL) 2(A$_2$pr)]-Leu-Arg-Pro-Gly-NH$_2$ and the corresponding D-A$_2$pr-containing isomer were prepared by reacting [D-Lys(DL-A$_2$pr)]LHRH (Preparation VA, 36 mg of the HCl salt) with bis(salicyl aldehydato)copper(II) (7 mg) [Y. Nakao and A. Nakahara, Bull. Chem. Soc. Japan, 46, 187 (1973)] in 90% aqueous DMF containing sodium acetate (4 mg) for 48 hours, then concentrated under vacuum to a small volume and subjected to HPLC. Purification is carried out on a Beckman HPLC system (Typ 142) using a 10×250 mm VYDAC Protein & Peptide C-18 column (300 A pore size, 5 m particle size) with a solvent system consisting of A: 0.1M ammonium acetate (pH 7), B: 0.1M ammonium acetate in 65% aqueous MeCN (referring to as system iii) in a linear gradient mode (15–45% B in 30 min) to yield the desired LHRH-peptide-copper-complex with L-A$_2$pr residue (8 mg) and D-A$_2$pr residue (9 mg), respectively. HPLC retention times for [D-Lys[(Cu++)(SAL)$_2$(L-A$_2$pr)]$^6$]LHRH and its D-A$_2$pr-containing isomer were 16.4 min and 17.8 min, respectively (solvent system iii, using linear gradient elution with 30–75% B in 30 min).

EXAMPLE VII

Peptide pGlu-His-Trp-Ser-Tyr-D-Lys[(Cu++)(SAL)$_2$(A$_2$pr)]-Leu-Arg-Pro-Gly-NH$_2$ was prepared as described in Example VI with the exception that [D-Lys(A$_2$pr)$^6$]LHRH (Preparation VIA, 36 mg of the HCl salt) was used in place of [D-Lys(DL-A$_2$pr)$^6$]LHRH. The desired product has HPLC retention time of 16.3 min.

EXAMPLE VIII

Peptide pGlu-His-Trp-Ser-Tyr-D-Lys[(Ni++)(SAL) 2(A$_2$pr)]-Leu-Arg-Pro-Gly-NH$_2$ and its D-A$_2$pr-containing isomer were prepared as described in Example VI with the exception that bis(salicyl aldehydato)nickel(II) (Aldrich, 7 mg) was used in place of bis(salicylaldehydato) copper(II). The crude product was purified by HPLC as described in Example VI to yield [D-Lys[(Ni++)(SAL)2(L-A$_2$pr)]$^6$]LHRH (7 mg) and [D-Lys[(Ni++)(SAL)2(D-A$_2$pr)]$^6$]LHRH (8 mg), having HPLC retention times of 17.5 min and 18.3 min, respectively.

EXAMPLE IX

The synthesis of peptide pGlu-His-Trp-Ser-Tyr-D-Lys[(Cu++)(CISAL)$_2$(DL-A$_2$pr)]-Leu-Arg-Pro-Gly-NH$_2$ was performed by reacting [D-Lys(DL-A$_2$pr)$^6$]LHRH (Preparation V, 36 mg) in DMF (0.2 ml) at pH 8 (adjusted with sodium hydroxide and sodium acetate) with 5-chloro-salicylaldehyde (4 mg) then, after standing at room temperature for 1 hour, with copper(II) acetate (3 mg in 0.05 ml water). The crude product was purified by HPLC under conditions given in Example VI to yield [D-Lys[(Cu++)(CISAL)2(DL-A$_2$pr)]$^6$]LHRH (16 mg, a mixture of the two diastereomers), having HPLC retention times of 23.5 min and 24.4 min when using solvent system iii in a linear gradient mode (30–75% B in 30 min).

EXAMPLE X

The synthesis of peptide pGlu-His-Trp-Ser-Tyr-D-Lys[(Ni++)(CISAL)$_2$(DL-A$_2$pr)]-Leu-Arg-Pro-Gly-NH$_2$ was accomplished as described in Example IX with the exception that [D-Lys(DL-A$_2$pr)$^6$]LHRH was reacted with nickel(II) acetate (3 mg) in place of copper(II) acetate. After purification by HPLC the product, [D-Lys[(Ni++)(CISAL)2(DL-A$_2$pr)]$^6$]LHRH (17 mg, a mixture of the two diastereomers) has retention times of 23.1 min. and 23.8 min.

EXAMPLE XI

Peptide Ac-D-Nal(2)-D-Phe(4Cl)-D-Pal(3)-Ser-Arg-D-Lys[(Cu++)(SAL)2(DL-A$_2$pr)]-Leu-Arg-Pro-D-Ala-NH$_2$ was prepared by reacting [Ac-D-Nal(2)$^1$,D-Phe(4Cl)$^2$,D-Pal(3)$^3$,Arg$^5$,D-Lys(DL-A$_2$pr)$^6$,D-Ala$^{10}$]LHRH (Preparation VIII, 40 mg of the TFA salt) in 80% aqueous DMF with bis(salicyl aldehidato)copper(II) (7 mg) in the presence of sodium acetate (4 mg) for 24 hours. The reaction mixture was then subjected to purification by HPLC with solvents A: 0.1M ammonium acetate (pH 7) and B: 0.1M ammonium acetate in 70% aqueous isopropanol (referred to as system iv below) using gradient elution (25–50% B in 35 min). Pure [Ac-D-Nal(2)$^1$,D-Phe(4Cl)$^2$,D-Pal(3)$^3$,Arg$^5$,D-Lys[(Cu++)(SAL)$^2$(DL-A$_2$pr)]$^6$,D-Ala$^{10}$]LHRH (38 mg) has a HPLC retention time of 9.5 min. when using solvent system iv in a linear gradient mode (45–90% B in 30 min).

EXAMPLE XII

Peptide Ac-D-Nal(2)-D-Phe(4Cl)-D-Trp-Ser-Arg-D-Lys[(Cu++)(SAL)$_2$(DL-A$_2$pr)]-Leu-Arg-Pro-D-Ala-NH$_2$ was prepared as described in Example XI with the exception that [Ac-D-Nal(2)$^1$,D-Phe(4Cl)$^2$,D-Trp$^3$,Arg$^5$,D-Lys(DL-A$_2$pr)$^6$,D-Ala$^{10}$]LHRH (Preparation VIII, 40 mg of a TFA salt) was used as starting material in place of the corresponding D-Pal(3)$^3$ analog to yield the desired compound, [Ac-D-Nal(2)$^1$,D-Phe(4Cl)$^2$,D-Trp$^3$,Arg$^5$,D-Lys[(Cu++)(SAL)$_2$(DL-A$_2$pr)]$^6$,D-Ala$^{10}$]LHRH (40 mg) with HPLC retention time of 11.7 min. under conditions given in Example XI.

EXAMPLE XIII

Peptide Ac-D-Nal(2)-D-Phe(4Cl)-D-Pal(3)-Ser-Arg-D-Lys[(Ni++)(SAL)$_2$(DL-A$_2$pr)]-Leu-Arg-Pro-D-Ala-NH$_2$ was prepared as described in Example XI with the exception that bis(salicylaldehydato)nickel(II) (7 mg) was used as complex forming agent in place of bis(salicylaldehydato) copper(II). The pure product, [Ac-D-Nal(2)$^1$,D-Phe(4Cl)$^2$,D-Pal(3)$^3$,Arg$^5$,D-Lys[(Ni++)(SAL)$_2$(DL-A$_2$pr)]$^6$,D-Ala$^{10}$]LHRH (34 mg) has HPLC retention time of 10.0 min. under conditions given in Example XI.

EXAMPLE XIV

Peptide pGlu-His-Trp-Ser-Tyr-D-Lys[(Cu++)-(SAL)$_2$(DL-A$_2$bu)]-Leu-Arg-Pro-Gly-NH$_2$ was prepared as described in Example VI with the exception that [D-Lys(DL-A$_2$bu)$^6$]LHRH (Preparation VB, 36 mg of the HCl salt) was used in place of [D-Lys(DL-A$_2$pr)$^6$]LHRH. The desired product has HPLC retention time of 17.7 min.

EXAMPLE XV

Peptide Ac-D-Nal(2)-D-Phe(4Cl)-D-Trp-Ser-Arg-D-Lys[(Ni++)(SAL)2(DL-A2pr)]-Leu-Arg-Pro-D-Ala-NH2 was prepared by reacting Ac-D-Nal(2)-D-Phe(4Cl)-D-Trp-Ser-Arg-D-Lys(DL-A2pr)-Leu-Arg-Pro-D-Ala-NH2 (Preparation VIIIB, 40 mg of the TFA salt) in 80% aqueous DMF with bis(salicylaldehydato)nickel(II) (7 mg) in the presence of sodium acetate (4 mg) for 24 hours. The reaction mixture was then subjected to purification by HPLC using solvent system iv in a linear gradient mode (30–50% B). The pure product, [Ac-D-Nal(2)$^1$,D-Phe(4Cl)$^2$,D-Trp$^3$,Arg$^5$,D-Lys[(Ni++)(SAL)2(DL-A2pr)]$^6$,D-Ala$^{10}$]LHRH (34 mg) has HPLC retention time of 11.1 min when using solvent system iv in a linear gradient mode as above.

EXAMPLE XVI pGlu-His-Trp-Ser-Tyr-D-Lys[(Cu++)(POLP)2(DL-A2bu)]-Leu-Arg-Pro-Gly-NH2 was prepared by reacting [D-Lys(DL-A2bu)$^6$]LHRH (Preparation VB, 36 mg of the HCl salt) in DMF (0.2 ml) at pH 8 (adjusted with sodium hydroxide and sodium acetate) with pyridoxal-5-phosphate monohydrate (Aldrich, 6 mg) then, after standing at room temperature for 1 hour, with copper-(II) acetate (3 mg in 0.05 ml water). The crude product was purified by HPLC using solvent system iii in a linear gradient mode (20–50% B) to yield [D-Lys[(Cu++)(POLP)2(DL-A2bu)$^6$]LHRH (18 mg) with a HPLC retention time of 6.8 min.

EXAMPLE XVII

Peptide pGlu-His-Trp-Ser-Tyr-D-Lys[(Cu++)(FUR)2(DL-A2pr)]-Leu-Arg-Pro-Gly-NH2 was prepared as described in Example IX with the exception that 2,5-dimethyl-4-hydroxy-3(2H)-furanone (Aldrich, 3 mg) was used in place of 5-chlorosalicylaldehyde. The product (15 mg) has HPLC retention time of 21.1 min.

EXAMPLE XVIII

Peptide pGlu-His-Trp-Ser-Tyr-D-Lys[Cu++)(POL)2(DL-A2pr)]-Leu-Arg-Pro-Gly-NH2 was prepared as described in Example IX with the exception that pyridoxal hydrochloride (Aldrich, 4 mg) was used in place of 5-chloro-salicylaldehyde. The DL-A2pr-containing product obtained (20 mg) has HPLC retention time of 11.2 min.

EXAMPLE XIX

Peptide pGlu-His-Trp-Ser-Tyr-D-Lys[Cu++)(POLP)2(A2pr)]-Leu-Arg-Pro-Gly-NH2 was prepared as described in Example XVI with the exception that [D-Lys(A2pr)$^6$]LHRH (Preparation VI, 36 mg) was used as starting material. [D-Lys[(Cu++)(POLP)2(A2pr)]$^6$]LHRH (20 mg), obtained has a HPLC retention time of 6.4 min.

EXAMPLE XX

Peptide Ac-D-Nal(2)-D-Phe(4Cl)-D-Pal(3)-Ser-Arg-D-Lys[(Cu++)(POLP)2(DL-A2pr)]-Leu-Arg-Pro-D-Ala-NH2 was prepared as described in Example XI with the exemption that pyridoxal 5-phosphate (Aldrich, 6 mg) was used in place of salicylaldehyde. The product has HPLC retention time of 5.4 min.

EXAMPLE XXI

Peptide pGlu-His-Trp-Ser-Tyr-D-Lys[(Cu++)(PEN)2(A2pr)]-Leu-Arg-Pro-Gly-NH2 was prepared by reacting [Lys(A2pr)$^6$]LHRH (Preparation VI, 36 mg) in DMF (0.2 ml) at pH 8 (adjusted with sodium hydroxide and sodium acetate) with methyl 2-oxo-cyclpentanecarboxylate (Aldrich, 3 mg) for 24 hour. Thereafter 0.04 ml 1M NaOH and copper(II) acetate (3 mg in 0.05 ml water) were added. The crude product was purified by HPLC in solvent system iii as in Example VI to yield [D-Lys[(Cu++)(PEN)2(A2pr)]$^6$]LHRH (15 mg) having HPLC retention time of 22.2 min when using solvent system iii in a linear gradient mode (30–75% B in 30 min).

EXAMPLE XXII

Peptide Ac-D-Nal(2)-D-Phe(4Cl)-D-Trp-Ser-Arg-D-Lys[(Cu++)(POLP)2(DL-A2pr)]-Leu-Arg-Pro-D-Ala-NH2 was prepared as described in Example XVI with the exception that [Ac-D-Nal(2)$^1$, D-Phe(4Cl)$^2$, D-Trp$^3$, Arg$^5$, D-Lys(DL-A2pr)$^6$, D-Ala$^{10}$]LHRH (Preparation VIII, 40 mg of a TFA salt) was used as starting material in place of [D-Lys(A$^2_p$r)$^6$]LHRH. The crude product was purified by HPLC using solvent system iv in a linear gradient mode (30–60% B) to give [Ac-D-Nal(2)$^1$, D-Phe(4Cl)$^2$,D-Trp$^3$, Arg$^5$,D-Lys[-(Cu++)(POLP)2(DL-A2pr)]$^6$,D-Ala$^{10}$]LHRH (35 mg) with HPLC retention time of 5.8 min).

EXAMPLE XXIII

The synthesis of peptide Ac-D-Nal(2)-D-Phe(4 Cl)-D-Trp-Ser-Arg-D-Lys[(Cu++)(POL)2(DL-A2pr)]-Leu-Arg-Pro-D-Ala-NH2 was performed by reacting [Ac-D-Nal(2)$^1$, D-Phe(4Cl)$^2$, D-Trp$^3$, Arg$^5$,D-Lys(DL-A2pr)$^6$, D-Ala$^{10}$]LHRH (Preparation VIII, 40 mg of a TFA salt) in DMF (0.2 ml) at pH 8 (adjusted with sodium hydroxide and sodium acetate) with pyridoxal hydrochloride (Aldrich, 4 mg) then, after standing at room temperature for 1 hour, with copper(II) acetate (3 mg in 0.05 ml water). The crude product was purified by HPLC under conditions given in Example XI (system iv) to yield [Ac-D-Nal(2)$^1$,D-Phe(4Cl)$^2$,D-Trp$^3$,Arg$^5$,D-Lys[(Cu++)(POL)2(DL-A2pr)]$^6$,D-Ala$^{10}$]LHRH (40 mg) with HPLC retention time of 6.3 min.

EXAMPLE XXIV

Peptide Ac-D-Nal(2)-D-Phe(4Cl)-D-Pal(3)-Ser-Arg-D-Lys[(Cu++)(POL)2(DL-A2pr)]-Leu-Arg-Pro-D-Ala-NH2 was prepared as described in Example XXIII with the exception that [Ac-D-Nal(2)$^1$,D-Phe(4Cl)$^2$, D-Pal(3)$^3$, Arg$^5$, D-Lys(DL-A2pr)$^6$, D-Ala$^{10}$]LHRH (Preparation VIII, 40 mg of the TFA salt) was used as starting material in place of the corresponding D-Trp$^3$ analog to yield the desired compound, [Ac-D-Nal(2)$^1$, D-Phe(4Cl)$^2$, D-Pal(3)$^3$, Arg$^5$, D-Lys[(Cu++)(POL)2(DL-A2pr)]$^6$, D-Ala$^{10}$]LHRH (35 mg) with HPLC retention time of 6.4 min.

EXAMPLE XXV

Peptide pGlu-His-Trp-Ser-Tyr-D-Lys[(Cu++)(POL)2(DL-A2bu)]-Leu-Arg-Pro-Gly-NH2 was prepared by reacting [D-Lys(DL-A2bu)$^6$]LHRH (Preparation VB, 36 mg of the HCl salt) in DMF (0.2 ml) at pH 8 (adjusted with sodium hydroxide and sodium acetate) with pyridoxal hydrochloride (Aldrich, 4 mg) then, after standing at room temperature for 1 hour, with copper(II) acetate (3 mg in 0.05 ml water). The crude product was purified by HPLC under conditions given in Example VI (solvent system iii) to yield the desired product with a HPLC retention time of 11.6 min (system iii).

EXAMPLE XXVI

Peptide pGlu-His-Trp-Ser-Tyr-D-Lys[(Cu++)-(SAL)$_2$(DL-A$_2$bu-Eac)-Leu-Arg-Pro-Gly-NH$_2$ was prepared as described in Example VI with the exception that [D-Lys(A$_2$pr)$^6$]LHRH (Preparation XB, 38 mg of the HCl salt) was used in place of [D-Lys(DL-A$_2$pr)$^6$]LHRH. The desired product has HPLC retention time of 10.4 min. under conditions given in Example VI.

EXAMPLE XXVII

Peptide Ac-D-Nal(2)-D-Phe(4Cl)-D-Pal(3)-Ser-Arg-D-Lys[(PtCl$_2$)-A$_2$bu-Eac)]-Leu-Arg-Pro-D-Ala-NH$_2$ was prepared as described in Example III with the exception that [Ac-D-Nal(2)$^1$, D-Phe(4Cl)$^2$, D-Pal(3)$^3$, Arg$^5$, D-Lys(A$_2$bu-Eac)$^6$,D-Ala$^{10}$]LHRH (Preparation XVB, 35 mg) was used as starting material in place of [D-Lys(A$_2$pr)$^6$]LHRH. The desired peptide Pt-complex obtained (10 mg.) has a HPLC retention time of 31.2 min under the conditions of Example III.

EXAMPLE XXVIII

Peptide Ac-D-Nal(2)-D-Phe(4Cl)-D-Pal(3)-Ser-Arg-D-Lys[(Cu++)(SAL)$_2$(A$_2$bu-Eac)]-Leu-Arg-Pro-D-Ala-NH$_2$ was prepared by reacting [Ac-D-Nal(2)$^1$,D-Phe(4Cl)$^2$,D-Pal(3)$^3$,Arg$^5$,D-Lys(A$_2$bu-Eac)$^6$,D-Ala$^{10}$]LHRH (Preparation XVB, 35 mg) in 80% aqueous DMF (0.2 ml) at pH 8 (adjusted with sodium hydroxide and sodium acetate) with salicylaldehyde (2.7 mg) then, after standing for 1 hour at room temperature, with copper acetate (4.2 mg in 0.05 ml water) for 24 hours. The reaction mixture was then subjected to purification by HPLC with solvents A: 0.1M ammonium acetate (pH 7) and B: isopropanol (referred to as system iv) using gradient elution (30–60% B in 45 min). Pure Ac-D-Nal(2)$^1$,D-Phe(4Cl)$^2$,D-Pal(3)$^3$,Arg$^5$,D-Lys[-(Cu++)(SAL)$^2$(A$_2$bu-Eac)$^6$,D-Ala$^{10}$]LHRH (25 mg) has a HPLC retention time of 11.0 min. when using solvent system iv in a linear gradient mode (45–90% B in 30 min).

EXAMPLE XXIX

The biological activities of and the receptor binding potencies of the claimed compounds are summarized in Table 1 to Table 3.

Table 1 shows the hormonal activity of the compounds of this invention having LHRH agonistic properties as compared to that of LHRH in dispersed rat pituitary cell superfusion system in vitro [S. Vigh and A. V. Schally, Peptides 5, 241–247 (1984)]. The peptide was infused for 3 minutes at various concentration, and the amount of LH released was compared to that released by 3 nM LHRH.

Table 2 presents the antiovulatory activity of the claimed compounds having LHRH-inhibiting properties. The inhibitory action was determined in vivo, in 4-day cycling rats as described [A. Corbin and C. W. Beattie, Endocr. Res. Commun., 2, 1–23 (1975)]. Affinities of the claimed compounds to membrane receptors of rat pituitary and human breast cancer cells are also given in Tables 1 and 2 as determined by using [$^{125}$I,D-Trp$^6$]LHRH.

EXAMPLE XXX

To obtain information about the cytotoxic properties of the compounds, the inhibition of $^3$H-thymidine incorporation into DNA of monolayer cultures of the rat mammary tumor cell line MT-4 was studied. Experiments started with 100K MT-4 cells/plate on day 0. Dose was changed 3 times, total incubation time with the sample was 5 days. 1 μCu $^3$H-thymidine/ml was added on day 4. Data obtained with the compound of Example VII (Table 3) indicate a strong inhibitory effect even at a concentration of $6 \times 10^{-10}$M.

TABLE 1

Hormonal activities and receptor binding potencies of agonistic analogues of LHRH containing cytostatic moieties.

| LHRH anal of Ex | Hormonal activity* LH responses rel. to LHRH (= 1) | Binding affinity, for membrane pituitary | $K_{a1}$, nM$^{-1}$** receptors of cancer cells |
|---|---|---|---|
| I | 133 | 10.697 | 6.244 |
| III | 55 | 3.285 | 1.743 |
| VIA | 12 | 3.051 | 1.348 |
| VII | 10 | 7.968 | 3.589 |
| VIIIA | 12 | 9.710 | 5.234 |
| VIIIB | 10 | 6.457 | 3.334 |
| IX | 10 | 8.625 | 3.995 |
| X | 4 | 4.513 | 2.236 |
| XIV | 25 | 5.589 | 1.628 |
| XVI | 1.5 | 9.751 | 5.038 |
| XVII | 10 | 1.770 | 0.536 |
| XVIII | 9 | 5.817 | 3.005 |
| XIX | 0.3 | 8.676 | 4.528 |
| XXI | 10.6 | 10.989 | 5.096 |
| XXV | 5.5 | 6.405 | 3.141 |

*LH responses to the analogues were determined in dispersed rat pituitary cell superfusion system.
**Affinity constants of the peptides for the first receptor class (i.e. for high affinity binding sites) of pituitary of male rats and human breast cancer cells, respectively, as determined by using $^{125}$I-labeled [D-Trp$^6$]LHRH.

TABLE 2

Hormonal activities and receptor binding potencies of antagonistic analogues of LHRH containing cytostatic moieties.

| LHRH analog of Ex | Hormonal Dose μg/rat | activity* % Blockade of ovulation | Binding affinity, for membrane pituitary | $K_{a1}$, nM$^{-1}$** receptors of cancer cells |
|---|---|---|---|---|
| II | 1.5 | 100 | 7.190 | 3.967 |
| XII | 3 | 20 | 9.183 | 4.951 |
| XIII | 1.5 | 100 | 1.821 | 0.878 |
| XV | 3 | 20 | 8.676 | 4.418 |
| XX | 3 | 80 | 5.250 | 2.436 |
| XXII | 10 | 60 | 2.901 | 1.337 |
| XXIII | 10 | 40 | 7.622 | 3.408 |
| XXIV | 3 | 50 | 5.483 | 2.628 |
| XXVII | | | | 2.152 |
| XXVIII | | | | 0.192 |

*LHRH-inhibiting potencies were assayed in 4-day cyclic rats.
**Affinity constants of the peptides for the first receptor class (i.e. for high affinity binding sites) of pituitary of male rats and human breast cancer cells, respectively, were determined by using $^{125}$I-labeled [D-Trp$^6$]LHRH.

TABLE 3

Affinities of the claimed peptides containing D-Mel$^6$ to membrane receptors of human prostate cancer and Dunning tumor

| LHRH anal | Human prostate cancer* | | Dunning tumor* | |
|---|---|---|---|---|
| | $K_{a1}$ nM$^{-1}$ | $K_{a2}$M$^{-1}$ | $K_{a1}$ nM$^{-1}$ | $K_{a2}$M$^{-1}$ |
| I | 9.66 | — | — | 5.73 |
| II | 0.7 | — | 1.68 | — |
| IIA | — | 0.97 | — | 25.14 |
| Control: | | | | |
| [D-Trp$^6$]- | 0.04 | — | 1.87 | — |

TABLE 3-continued

Affinities of the claimed peptides containing D-Mel[6] to membrane receptors of human prostate cancer and Dunning tumor

| LHRH | Human prostate cancer* | | Dunning tumor* | |
|---|---|---|---|---|
| analog | $K_{a1} nM^{-1}$ | $K_{a2} M^{-1}$ | $K_{a1} nM^{-1}$ | $K_{a2} M^{-1}$ |
| LHRH | | | | |

*Affinity constants of the peptides for the first receptor class, $K_{a1}$ (i.e. for high affinity binding sites) and for the second receptor class, $K_{a2}$ (i.e. for low affinity binding sites) of human prostate cancer and rat Dunning tumor, respectively, as determined by using $^{125}$I-labeled [D-Trp$^6$]LHRH.

TABLE 4

Inhibitory effect of compound of Example VII on $^3$H-Thymidine incorporation into DNA

| Dose ng/ml | DME Medium + 10% Serum DPM/Well[b] | | DME Medium + 0% Serum[a] DPM/Well[b] | |
|---|---|---|---|---|
| | × 1000 | % Inhibition | × 1000 | % Inhibition |
| 0 | 102 +/− 20.3 | — | 421 +/− 15 | — |
| 1[c] | 48 +/− 8.6 | 53 | 249 +/− 30.5 | 41 |
| 10 | 40 +/− 6.7 | 61 | 242 +/− 32.1 | 42 |
| 100 | 42 +/− 10.4 | 59 | 186 +/− 13.2 | 56 |
| 1000 | 36 +/− 5.1 | 65 | 204 +/− 40.9 | 52 |
| 2000 | 39 +/− 4.6 | 62 | 249 +/− 45.1 | 41 |

[a]DME medium plus additives, no serum added.
[b]Mean +/− standard error;
* = .05,
** = .01 by Duncan's new multiple range test.
[c]corresponds to $6 \times 10^{-10}$ M

We claim:

1. A compound selected from the group consisting of:
   a) pGlu-His-Trp-Ser-Tyr-D-Lys[(PtCl$_2$)(DL-A$_2$pr)]-Leu-Arg-Pro-Gly-NH$_2$;
   b) pGlu-His-Trp-Ser-Tyr-D-Lys[(Cu++)(SAL)$_2$(D-A$_2$pr)]-Leu-Arg-Pro-Gly-NH$_2$;
   c) pGlu-His-Trp-Ser-Tyr-D-Lys[(Cu++)(POL)$_2$(DL-A$_2$pr)]-Leu-Arg-Pro-Gly-NH$_2$;
   d) pGlu-His-Trp-Ser-Tyr-D-Lys[(Cu++)(PEN)$_2$(A$_2$pr)]-Leu-Arg-Pro-Gly-NH$_2$;
   e) Ac-D-Nal(2)-D-Phe(4Cl)-D-Pal(3)-Ser-Arg-D-Lys[(Ni++)(SAL)$_2$(DL-A$_2$pr)]-Leu-Arg-Pro-D-Ala-NH$_2$;
   f) Ac-D-Nal(2)-D-Phe(4Cl)-D-Trp-Ser-Arg-D-Lys[(Cu++)(POLP)$_2$(DL-A$_2$pr)]-Leu-Arg-Pro-D-Ala-NH$_2$;
   g) Ac-D-Nal(2)-D-Phe(4Cl)-D-Trp-Ser-Arg-D-Lys[(Cu++)(POL)$_2$(DL-A$_2$pr)]-Leu-Arg-Pro-D-Ala-NH$_2$; and
   h) Ac-D-Nal(2)-D-Phe(4Cl)-D-Pal(3)-Ser-Arg-D-Lys[(Cu++)(POL)$_2$(DL-A$_2$pr)]-Leu-Arg-Pro-D-Ala-NH$_2$.

2. The compound of claim 1 being pGlu-His-Trp-Ser-Tyr-D-Lys[(PtCl$_2$)(DL-A$_2$pr)]-Leu-Arg-Pro-Gly-NH$_2$.

3. The compound of claim 1 being pGlu-His-Trp-Ser-Tyr-D-Lys[(Cu++)(SAL)$_2$(D-A$_2$pr)]-Leu-Arg-Pro-Gly-NH$_2$.

4. The compound of claim 1 being Ac-D-Nal(2)-D-Phe(4Cl)-D-Pal(3)-Ser-Arg-D-Lys[(NI++)-(SAL)$_2$(DL-A$_2$pr)]-Leu-Arg-Pro-D-Ala-NH$_2$.

5. The compound of claim 1 being Ac-D-Nal(2)-D-Phe(4Cl)-D-Trp-Ser-Arg-D-Lys[(Cu++)-(POLP)$_2$(DL-A$_2$pr)]-Leu-Arg-Pro-D-Ala-NH$_2$.